United States Patent [19]

Sugiyama et al.

[11] Patent Number: 5,308,840
[45] Date of Patent: May 3, 1994

[54] SUBSTITUTED OR UNSUBSTITUTED BENZHYDRYL HETEROALKYL-SUBSTITUTED AMINOPHENOL COMPOUNDS AND PHARMACEUTICAL COMPOSITIONS THEREOF

[75] Inventors: Naoki Sugiyama; Fumihiko Akaboshi; Haruko Yakumaru; Tomokazu Gotoh; Masanori Sugiura; Shigeki Kuwahara; Masahiko Kajii; Yoshiko Tanaka; Takao Kondoh; Chikara Fukaya, all of Hirakata, Japan

[73] Assignee: Green Cross Corporation, Osaka, Japan

[21] Appl. No.: 863,752

[22] Filed: Apr. 6, 1992

[30] Foreign Application Priority Data

Apr. 8, 1991 [JP] Japan .................. 3-103886
Jul. 26, 1991 [JP] Japan .................. 3-209920

[51] Int. Cl.$^5$ ............... A61K 31/435; A61K 31/495; A61K 31/55; C07D 295/13
[52] U.S. Cl. ..................... 514/212; 514/218; 514/252; 514/255; 514/318; 514/327; 514/331; 540/575; 540/597; 540/604; 540/609; 544/34; 544/41; 544/360; 544/383; 544/396; 544/397; 546/194; 546/216; 546/232; 546/333; 546/334
[58] Field of Search ............. 540/450, 481, 482, 470, 540/575, 597, 604, 609; 544/360, 383, 396, 397; 546/196, 216, 232; 514/183, 212, 218, 252, 255, 318, 327, 331, 340

[56] References Cited

U.S. PATENT DOCUMENTS 4,929,618  5/1990  Koda et al. ............ 514/327
5,028,610  7/1991  Hirai et al. ............ 544/397
5,070,087  12/1991  Teng et al. ............ 514/212

FOREIGN PATENT DOCUMENTS 0031910  7/1981  European Pat. Off. .
0228893  7/1987  European Pat. Off. .
2610501  9/1977  Fed. Rep. of Germany .
2453854  11/1980  France .
2056968  3/1981  United Kingdom .

OTHER PUBLICATIONS

Teraji et al., CA 95:150706K (1981).
Carlson et al., Agents and Actions, vol. 26, No. 314, pp. 319–328 (1989).
Uchiyama et al., Analytical Biochemistry, vol. 86, pp. 271–278 (1978).

*Primary Examiner*—Mukund J. Shah
*Assistant Examiner*—Philip Datlow
*Attorney, Agent, or Firm*—Sughrue, Mion, Zinn, Macpeak & Seas

[57] ABSTRACT

Aminophenol derivatives of the following formula (I)

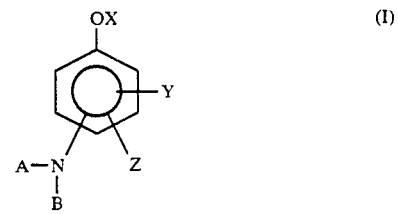

wherein X is hydrogen atom, lower alkyl or a protecting group for phenolic hydroxy, Y is hydrogen atom or lower alkyl, Z is hydrogen atom, lower alkyl, halogen atom or trifluoromethyl, A is hydrogen atom or lower alkyl, t is an integer of 1 to 5, l and m are respectively an integer of 2 to 4, E and W are nitrogen atoms, F is a direct bond or oxygen atom, P and Q are each hydrogen atom, halogen atom, lower alkyl or lower alkoxy, and $R^8$ is hydrogen atom, hydroxy or a hydroxy-protecting group, and their pharmcologically acceptable salts. Since the aminophenol derivatives (I) of the present invention have excellent antioxidative action and antiinflammatory and antiallergic action in mammalian animals including human, they are extremely useful as pharmaceuticals such as an antiinflammatory or an antiallergic.

7 Claims, No Drawings

SUBSTITUTED OR UNSUBSTITUTED BENZHYDRYL HETEROALKYL-SUBSTITUTED AMINOPHENOL COMPOUNDS AND PHARMACEUTICAL COMPOSITIONS THEREOF

FIELD OF THE INVENTION

The present invention relates to novel aminophenol derivatives (hereinafter sometimes referred to as aminophenol derivatives (I)) which are useful as pharmaceuticals, their pharmacologically acceptable salts, and pharmaceutical compositions containing same as an active ingredient.

BACKGROUND OF THE INVENTION

Active oxygens produced by various cells and tissues such as leukocytes have recently received increased attention as new mediators. The active oxygen includes superoxide anions ($.O_2^-$), hydrogen peroxides ($H_2O_2$), hydroxy radicals ($.OH^-$), and singlet oxygens ($^1O_2$), and in a wider sense, it includes peroxy radicals (LOO.), alkoxy radicals (LO.), and lipoperoxides (LOOH).

The active oxygen is a self-defensive factor, and is a tissue disorder factor as well. It has been clarified that tissue disorder attributable to excessive production of active oxygen causes autoimmune diseases, inflammatory diseases, circulatory diseases, and gastrointestinal diseases.

Therefore, it is expected that a compound which contributes to inhibition of the production of active oxygens, or trapping of active oxygens should be useful as a pharmaceutical.

While there have been so far developed various pharmaceuticals which inhibit production of active oxygens, or trap active oxygens, no satisfactory pharmaceuticals have been actually developed.

SUMMARY OF THE INVENTION

An object of the present invention is to provide novel aminophenol derivatives which markedly inhibit production of active oxygens, or trap active oxygens (antioxidative action), and are useful particularly as a pharmaceutical such as antiinflammatory and antiallergy, and pharmacologically acceptable salts thereof.

The present inventors have conducted intensive studies for the purpose of producing a compound which markedly inhibits production of active oxygens, or traps active oxygens (antioxidative action), and found that some novel compounds possess superior actions of inhibiting production of active oxygens, or trapping active oxygens (antioxidative action). Moreover, they have found that said compounds possess antiinflammatory, and antiallergic actions besides the above-mentioned actions. Further studies resulted in the production of a novel compound useful as a pharmaceutical such as antiinflammatory and antiallergic.

The present invention relates to aminophenol derivatives (I) of the following formula

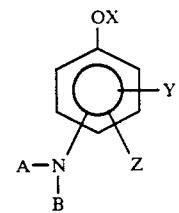

(I)

wherein X is hydrogen atom, lower alkyl or a protecting group for phenolic hydroxy, Y is $Y^1$—$Y^3$, Z is hydrogen atom, lower alkyl, halogen atom or trifluoromethyl, A is $A^1$—$A^5$, B is $B^1$—$B^5$ with the proviso that when A is $A^1$, B is $B^1$ and Y is $Y^1$ or $Y^2$, when A is $A^2$, B is $B^2$ and Y is $Y^3$, when A is $A^3$, B is $B^3$ and Y is $Y^3$, when A is $A^4$, B is $B^4$ and Y is $Y^3$, and when A is $A^5$, B is $B^5$ and Y is $Y^3$; wherein when A is $A^1$, B is $B^1$ and Y is $Y^1$, $A^1$ and $B^1$ are the same or different and each is hydrogen atom, lower alkyl, or $A^1$ and $B^1$ may combinedly form an alkylene having 2 to 5 carbon atoms, and $Y^1$ is of the formula

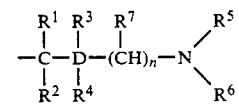

wherein n is an integer of 1 to 4, $R^1$ is $R^{1A}$—$R^{1E}$, $R^2$ is $R^{2A}$—$R^{2E}$, $R^3$ is $R^{3A}$—$R^{3E}$, $R^4$ is $R^{4A}$—$R^{4E}$, $R^5$ is $R^{5A}$—$R^{5E}$, $R^6$ is $R^{6A}$—$R^{6E}$, $R^7$ is $R^{7A}$—$R^{7E}$, and D is oxygen atom, nitrogen atom or carbon atom, with the proviso that when D is oxygen atom, $R^1$—$R^7$ is $R^{1A}$—$R^{7A}$, when D is nitrogen atom, $R^1$—$R^7$ is $R^{1B}$—$R^{7B}$ or $R^{1C}$—$R^{7C}$, and when D is carbon atom, $R^1$—$R^7$ is $R^{1D}$—$R^{7D}$ or $R^{1E}$—$R^{7E}$, wherein when D is oxygen atom, $R^{1A}$ is phenyl or pyridyl (these groups may have substituents), $R^{2A}$ is hydrogen atom or lower alkyl, $R^{3A}$ and $R^{4A}$ are absent, $R^{5A}$—$R^{7A}$ are the same or different and each is hydrogen atom, lower alkyl or two optionally selected from $R^{5A}$—$R^{7A}$ may form an alkylene having 2 to 5 carbon atoms, when D is nitrogen atom, $R^{1B}$ is phenyl or pyridyl (these groups may have substituents), $R^{2B}$ is hydrogen atom or lower alkyl, $R^{3B}$ is absent, $R^{4B}$—$R^{7B}$ are the same or different and each is hydrogen atom, lower alkyl or two optionally selected &rom $R^{4B}$—$R^{7B}$ may form an alkylene having 2 to 5 carbon atoms, or $R^{1C}$ and $R^{2C}$ are the same or different and each is hydrogen atom or lower alkyl, $R^{3C}$ is absent, $R^{4C}$ is phenyl or pyridyl (these groups may have substituents), $R^{5C}$—$R^{7C}$ are the same or different and each is hydrogen atom, lower alkyl or two optionally selected from $R^{5C}$—$R^{7C}$ may form an alkylene having 2 to 5 carbon atoms, and when D is carbon atom, $R^{1D}$ is phenyl or pyridyl (these groups may have substituents), $R^{2D}$—$R^{4D}$ are the same or different and each is hydrogen atom or lower alkyl, $R^{5D}$—$R^{7D}$ are the same or different and each is hydrogen atom, lower alkyl or two optionally selected from $R^{5D}$—$R^{7D}$ may form an alkylene having 2 to 5 carbon atoms, or $R^{1E}$ is phenyl, pyridyl, benzyl or pyridylmethyl (these groups may have substituents), $R^{2E}$ and $R^{3E}$ may form a single bond, $R^{4E}$ is hydrogen atom or lower alkyl, $R^{5E}$—$R^{7E}$ are the same or different and each is hydrogen atom, lower alkyl or two optionally selected from $R^{5E}$—$R^{7E}$ may form an alkylene having 2 to 5 carbon atoms;

when A is $A^1$, B is $B^1$ and Y is $Y^2$, $A^1$ and $B^1$ are as defined above, and $Y^2$ is of the formula

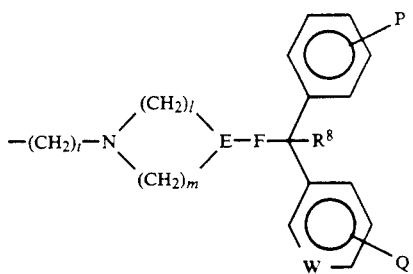

wherein t is an integer of 1 to 5, l and m are respectively an integer of 2 to 4, E and W are the same or different and each is nitrogen atom or CH, F is a direct bond or oxygen atom, P and Q are the same or different and each is hydrogen atom, halogen atom, lower alkyl or lower alkoxy, and $R^8$ is hydrogen atom, hydroxyl group or a hydroxy-protecting group;

when A is $A^2$, B is $B^2$, Y is $Y^3$, $Y^3$ is hydrogen atom or lower alkyl, $A^2$ is phenyl, pyridyl, benzyl or pyridylmethyl (these groups may have substituents), and $B^2$ is of the formula

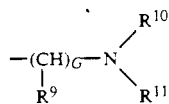

wherein G is an integer of 1 to 3, $R^9$—$R^{11}$ are the same or different and each is hydrogen atom, lower alkyl, or two optionally selected from $R^9$—$R^{11}$ may form an alkylene having 2 to 5 carbon atoms;

when A is $A^3$, B is $B^3$, and Y is $Y^3$, $Y^3$ is as defined above, $A^3$ is hydrogen atom, lower alkyl, or $A^3$ and $R^{12}$ may form an alkylene having 2 to 5 carbon atoms, and $B^3$ is of the formula

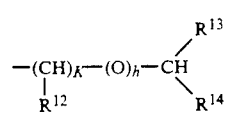

wherein K is an integer of 1 to 3, h is 0 or 1, $R^{12}$ is hydrogen atom, lower alkyl, or $R^{12}$ and $A^3$ may form an alkylene having 2 to 5 carbon atoms, and $R^{13}$ and $R^{14}$ are the same or different and each is phenyl or pyridyl (these groups may have substituents);

when A is $A^4$, B is $B^4$, and Y is $Y^3$, $Y^3$ is as defined above, $A^4$ is hydrogen atom, lower alkyl or $A^4$ and V may together with the adjacent nitrogen atom form a 4–6-membered ring, and $B^4$ is of the formula

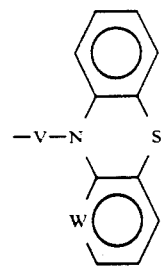

wherein V is alkylene, or V and $A^4$ may together with the adjacent nitrogen atom form a 4–6-membered ring, and W is a nitrogen atom or CH; and when A is $A^5$, B is $B^5$, and Y is $Y^3$, $Y^3$ is as defined above, $A^5$ is hydrogen atom or lower alkyl, and $B^5$ is of the formula

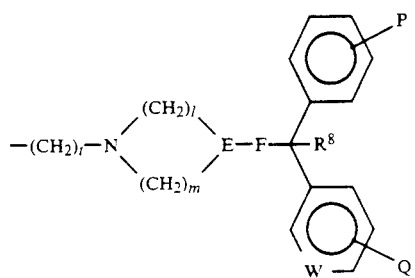

wherein each symbol is as defined above; and their pharmacologically acceptable salts.

The aminophenol derivatives (I) of the present invention can be classified into, for example, the following compounds of Groups A to J.

(1) Compounds wherein A is $A^1$, B is $B^1$, Y is $Y^1$, D is oxygen atom, and $R^1$—$R^7$ are $R^{1A}$—$R^{7A}$ (hereinafter sometimes referred to as Group A)

Aminophenol derivatives of the formula

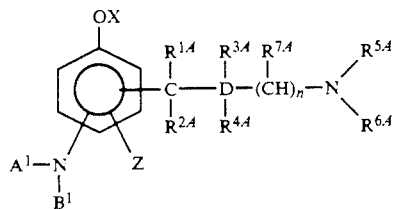

wherein $A^1$ and $B^1$ are the same or different and each is hydrogen atom, lower alkyl or $A^1$ and $B^1$ may form an alkylene having 2 to 5 carbon atoms, n is an integer of 1 to 4, $R^{1A}$ is phenyl or pyridyl (these groups may have substituents), $R^{2A}$ is hydrogen atom or lower alkyl, $R^{3A}$ and $R^{4A}$ are absent, $R^{5A}$—$R^{7A}$ are the same or different and each is hydrogen atom, lower alkyl, or two optionally selected from $R^{5A}$—$R^{7A}$ may form an alkylene having 2 to 5 carbon atoms, and other symbols are as defined above, and their pharmacologically acceptable salts.

(2) Compounds wherein A is $A^1$, B is $B^1$, Y is $Y^1$, D is nitrogen atom, and $R^1$—$R^7$ are $R^{1B}$—$R^{7B}$ (hereinafter sometimes referred to as Group B)

Aminophenol derivatives of the formula

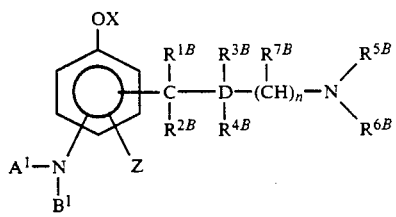

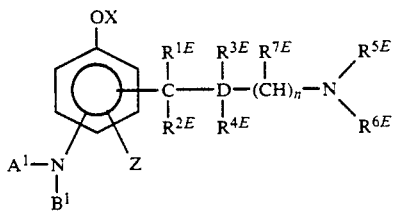

wherein $R^{1B}$ is phenyl or pyridyl (these groups may have substituents), $R^{2B}$ is hydrogen atom or lower alkyl, $R^{3B}$ is absent, $R^{4B}$—$R^{7B}$ are the same or different and each is hydrogen atom, lower alkyl, or two optionally selected from $R^{4B}$—$R^{7B}$ may form an alkylene having 2 to 5 carbon atoms, and other symbols are as defined above, and their pharmacologically acceptable salts.

(3) Compounds wherein A is $A^1$, B is $B^1$, Y is $Y^1$, D is nitrogen atom, and $R^1$—$R^7$ are $R^{1C}$—$R^{7C}$ (hereinafter sometimes referred to as Group C)

Aminophenol derivatives of the formula

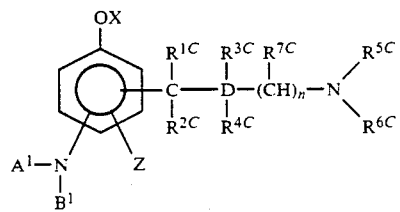

wherein $R^{1C}$ and $R^{2C}$ are the same or different and each is hydrogen atom or lower alkyl, $R^{3C}$ is absent, $R^{4C}$ is phenyl or pyridyl (these groups may have substituents), $R^{5C}$—$R^{7C}$ are the same or different and each is hydrogen atom, lower alkyl, or two optionally selected from $R^{5C}$—$R^{7C}$ may form an alkylene group having 2 to 5 carbon atoms, and other symbols are as defined above, and their pharmacologically acceptable salts.

(4) Compounds wherein A is $A^1$, B is $B^1$, Y is $Y^1$, D is carbon atom, and $R^1$—$R^7$ are $R^{1D}$—$R^{7D}$ (hereinafter sometimes referred to as Group D)

Aminophenol derivatives of the formula

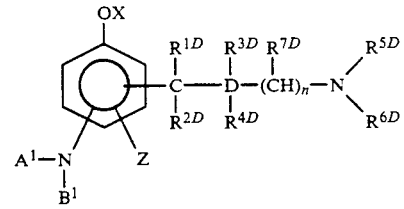

wherein $R^{1D}$ is phenyl or pyridyl (these groups may have substituents), $R^{2D}$—$R^{4D}$ are the same or different and each is hydrogen atom or lower alkyl, $R^{5D}$—$R^{7D}$ are the same or different and each is hydrogen atom, lower alkyl, or two optionally selected from $R^{5D}$—$R^{7D}$ may form an alkylene having 2 to 5 carbon atoms, and other symbols are as defined above, and their pharmacologically acceptable salts.

(5) Compounds wherein A is $A^1$, B is $B^1$, Y is $Y^1$, D is carbon atom, and $R^1$—$R^7$ are $R^{1E}$—$R^{7E}$ (hereinafter sometimes referred to as Group E)

Aminophenol derivatives of the formula wherein $R^{1E}$ is phenyl, pyridyl, benzyl or pyridylmethyl (these groups may have substituents), $R^{2E}$ and $R^{3E}$ may form a single bond, $R^{4E}$ is hydrogen atom or lower alkyl, $R^{5E}$—$R^{7E}$ are the same or different and each is hydrogen atom, lower alkyl, or two optionally selected from $R^{5E}$—$R^{7E}$ may form an alkylene having 2 to 5 carbon atoms, and other symbols are as defined above, and their pharmacologically acceptable salts.

(6) Compounds wherein A is $A^1$, B is $B^1$, Y is $Y^2$ (hereinafter sometimes referred to as Group F)

Aminophenol derivatives of the formula

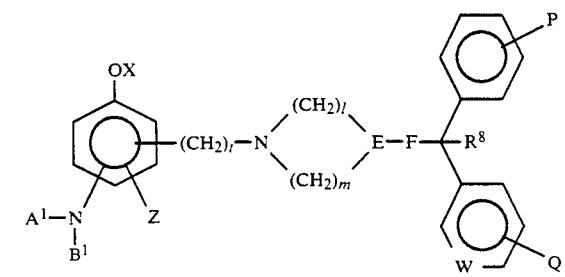

wherein t is an integer of 1 to 5, l and m are respectively an integer of 2 to 4, E and W are the same or different and each is nitrogen atom or CH, F is a direct bond or oxygen atom, P and Q are the same or different and each is hydrogen atom, halogen atom, lower alkyl, or lower alkoxy, $R^8$ is hydrogen atom, hydroxyl group, or a hydroxy-protecting group, and other symbols are as defined above, and their pharmacologically acceptable salts.

(7) Compounds wherein A is $A^2$, B is $B^2$, Y is $Y^3$ (hereinafter sometimes referred to as Group G)

Aminophenol derivatives of the formula

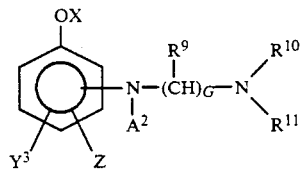

wherein $A^2$ is phenyl, pyridyl, benzyl or pyridylmethyl (these groups may have substituents), G is an integer of 1 to 3, $R^9$—$R^{11}$ are the same or different and each is hydrogen atom, lower alkyl or two optionally selected from $R^9$—$R^{11}$ may form an alkylene group having 2 to 5 carbon atoms, $Y^3$ is hydrogen atom or lower alkyl, and other symbols are as defined above, and their pharmacologically acceptable salts.

(8) Compounds wherein A is $A^3$, B is $B^3$, Y is $Y^3$ (hereinafter sometimes referred to as Group H)

Aminophenol derivatives of the formula

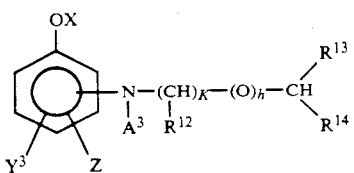

wherein $A^3$ is hydrogen atom, lower alkyl, or $A^3$ and $R^{12}$ may form an alkylene group having 3 to 5 carbon atoms, K is an integer of 1 to 3, h is 0 or 1, $R^{12}$ is hydrogen atom, lower alkyl or $R^{12}$ and $A^3$ may form an alkylene group having 2 to 5 carbon atoms, $R^{13}$ and $R^{14}$ are the same or different and each is phenyl or pyridyl (these groups may have substituents), and other symbols are as defined above, and their pharmacologically acceptable salts.

(9) Compounds wherein A is $A^4$, B is $B^4$, Y is $Y^3$ (hereinafter sometimes referred to as Group I)

Aminophenol derivatives of the formula

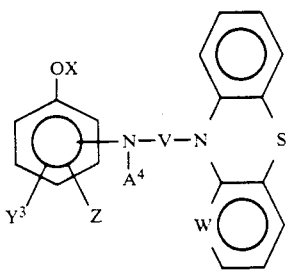

wherein $A^4$ is hydrogen atom, lower alkyl, or $A^4$ and V may together with the adjacent nitrogen atom form a 4-6-membered ring, V is alkylene, or V and $A^4$ may together with the adjacent nitrogen atom form a 4-6-membered ring, W is nitrogen atom or CH, and other symbols are as defined above, and their pharmacologically acceptable salts.

(10) Compounds wherein A is $A^5$, B is $B^5$, Y is $Y^3$ (hereinafter sometimes referred to as Group J)

Aminophenol derivatives of the formula

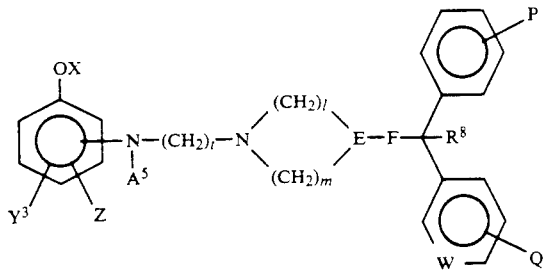

wherein $A^5$ is hydrogen atom or lower alkyl, and other symbols are as defined above, and their pharmacologically acceptable salts.

In the present specification, the lower alkyl may be straight- or branched-chain, and is exemplified by those having 1 to 10 carbon atoms, preferably 1 to 8 carbon atoms, such as methyl, ethyl, propyl, isopropyl, butyl, isobutyl, sec-butyl, tert-butyl, pentyl, hexyl, and octyl.

The protecting group for phenolic hydroxy includes acetyl, benzyl, and methoxymethyl.

The hydroxy-protecting group includes lower alkyl, acetyl, and methoxymethyl.

The pyridyl may be 2-, 3-, or 4-pyridyl.

The phenyl and pyridyl may be substituted by halogen atom, lower alkyl, or lower alkoxy, at preferably para-position, although no particular limitation is posed on the binding site.

The halogen atom includes fluorine, chlorine, bromine, and iodine.

The lower alkoxy may be straight- or branched-chain, and preferably exemplified by those having 1 to 4 carbon atoms, such as methoxy, ethoxy, propoxy, isopropoxy, butoxy, isobutoxy, sec-butoxy, and tert-butoxy.

The benzyl and pyridylmethyl may be substituted by the same group as for phenyl and pyridyl at preferably para-position, although no particular limitation is posed on the binding site.

The alkylene group having 2 to 5 carbon atoms may be straight- or branched-chain, and is exemplified by ethylene, trimethylene, propylene, tetramethylene, pentamethylene, 1-methylethylene, 1-methyltetramethylene, and 2-methyltetramethylene.

In the present specification, forming a single bond with $R^{2E}$ and $R^{3E}$ means forming a double bond with C and D such as in $R^{1E}-C=D-R^{4E}$.

or Y may be bound at any position relative to OX of formula (I). However,

is preferably bound at the ortho-position and Y is preferably bound at the para-position relative to the OX.

The preferable compounds of the present invention are those of Group J mentioned above. When the aminophenol derivatives (I) of the present invention have asymmetric carbon atoms, optical isomers thereof and the mixture of the optical isomers are included in the scope of the present invention.

The pharmacologically acceptable salts of the aminophenol derivatives (I) of the present invention include, for example, inorganic acid addition salts such as hydrochloride, hydrobromide, and sulfate, and organic acid addition salts such as acetate, oxalate and benzenesulfonate.

The aminophenol derivatives (I) of the present invention can be produced by various methods. The methods for production are exemplified in the following.

Method 1: Compounds of Group A

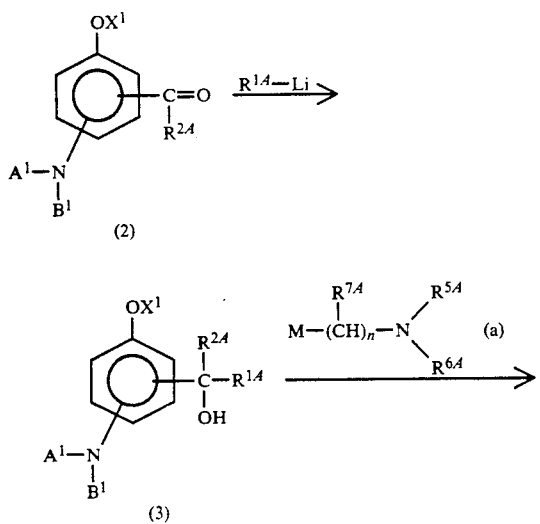

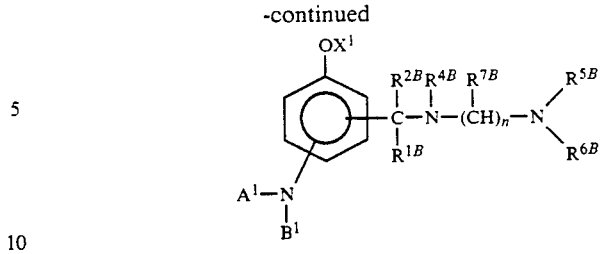

wherein each symbol is as defined above.

Compound (3) is used in the present reaction after being converted to a leaving group by a known means such as halogenation, mesylation, acetylation, etc.

The reaction proceeds at 0° C. to room temperature for 30 minutes to 5 hours.

A compound of Group B thus obtained can be converted to a compound without a protecting group as desired by eliminating the protecting group for phenolic hydroxy by a means known per se.

Method (3): Compounds of Group C

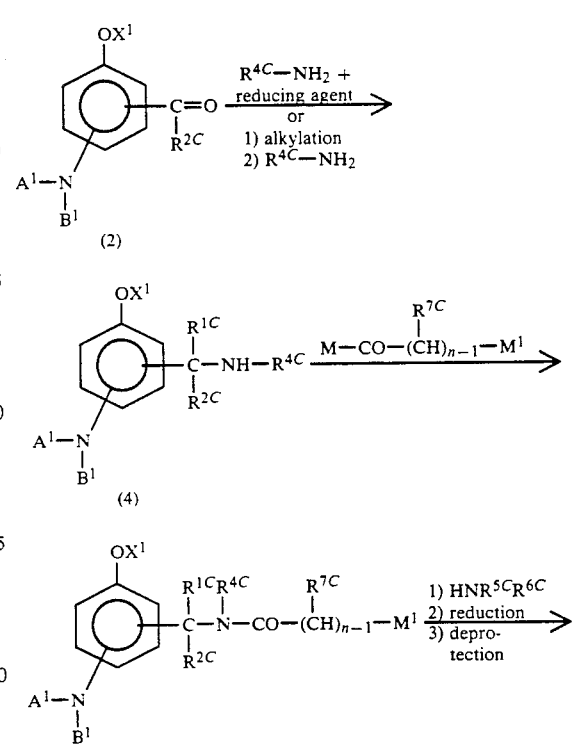

wherein $X^1$ is a protecting group for phenolic hydroxy, M is a reactive group such as halogen, and other symbols are as defined above.

Compound (3) can be produced by reacting compound (2) with $R^{1A}$—Li in a solvent such as tetrahydrofuran at a low temperature for 30 minutes to 5 hours.

The $R^{1A}$—Li is produced by reacting $R^{1A}$ (e.g. benzene or pyridine having bromine) with butyllithium.

A compound of Group A can be produced by, for example, reacting compound (3) and compound (a) in the presence of a phase transfer catalyst such as tetrabutylammonium hydrogensulfate at room temperature for 10 to 60 hours.

The compound of Group A thus obtained can be converted to a compound without a protecting group as desired by eliminating the protecting group for phenolic hydroxy by a means known per se.

Method (2): Compounds of Group B

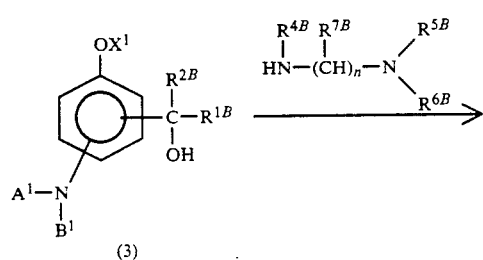

wherein each symbol is as defined above.

When either or both of $R^{1c}$ and $R^{2c}$ is (are) hydrogen atom(s), compound (2) is reacted with amine ($R^{4c}$—$NH_2$), and reduced by a reducing agent such as sodium cyanoborohydride.

This reaction is conducted in a solvent such as methanol at room temperature for 10 minutes to 6 hours, thereby to give compound (4).

When both of $R^{1c}$ and $R^{2c}$ are lower alkyls, compound (2) is subjected to alkylation using alkyllithium to give an alcohol compound, and therefrom is produced compound (4) according to Method (2).

Then, an amide compound is produced by an reaction in the presence of a base such as potassium carbonate at room temperature for about 1 hour.

Thereafter, the obtained amide compound is reacted with amine ($HNR^{5c}R^{6c}$), followed by reduction of carbonyl with a reducing agent such as borane-methyl sulfide in an inert gas.

The compound thus obtained can be converted to a compound without a protecting group as desired by eliminating the protecting group for phenolic hydroxy by a means known per se.

Method (4): Compounds of Group D and Group E

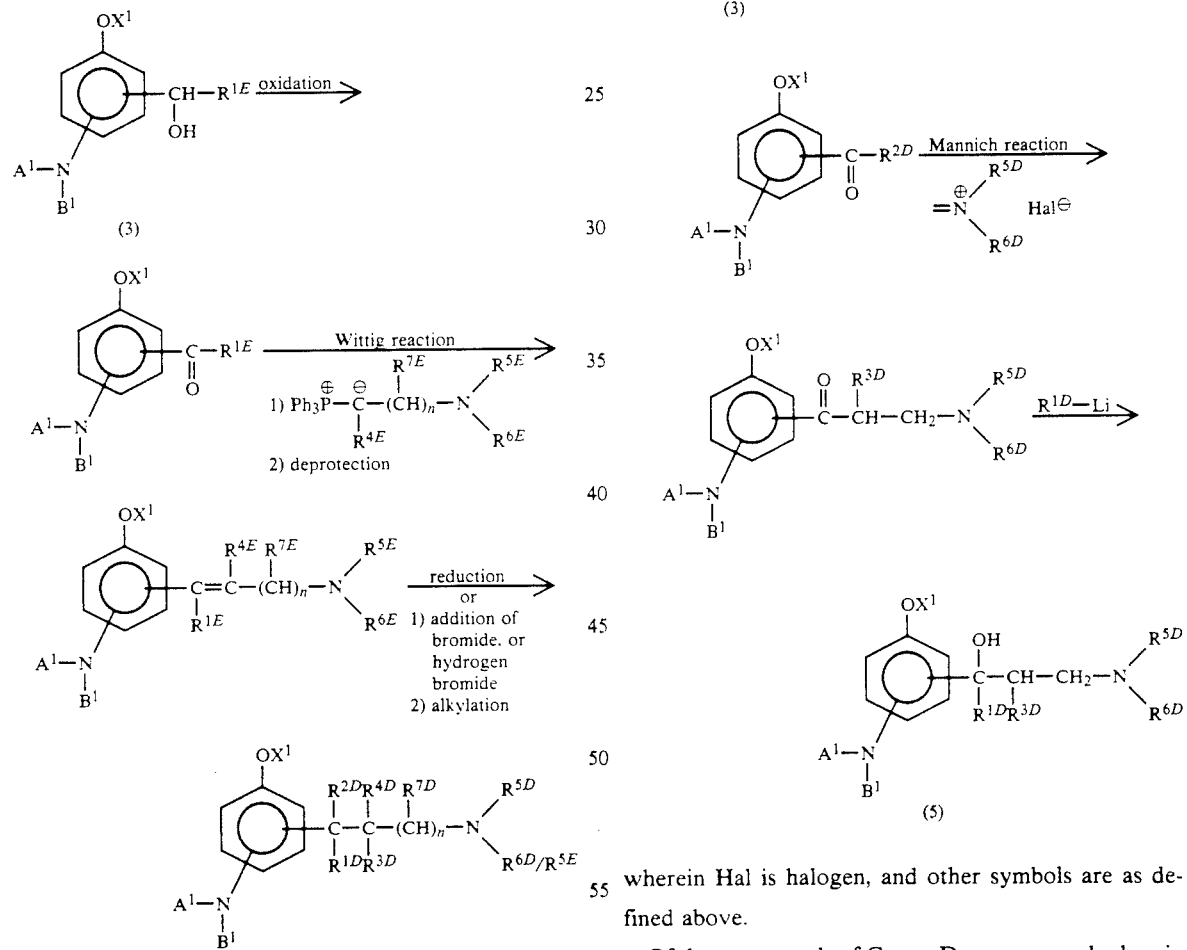

wherein each symbol is a defined above.

A compound of group E can be obtained by treating compound (3) with an oxidizing agent such as Jones reagent to give a ketone compound, and subjecting the ketone compound to Wittig reaction. The Wittig reaction can be conducted by reacting without solvent or in a solvent such as benzene preferably under reflux for 1 hour to 1 day.

The compound thus obtained can be converted to a compound of Group E without a protecting group as desired by eliminating the protecting group for phenolic hydroxy by a means known per se.

A compound of Group D can be obtained by reduction of a compound of Group E in the presence of platinum oxide catalyst or by bromination or hydrobromination of a compound of Group E followed by alkylation using alkyllithium.

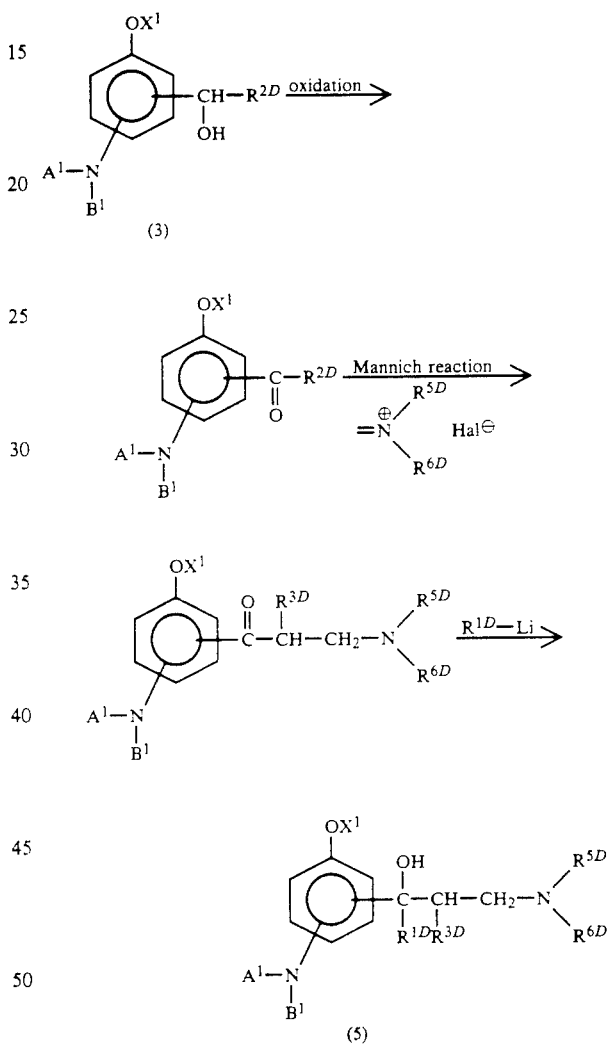

wherein Hal is halogen, and other symbols are as defined above.

Of the compounds of Group D, a compound wherein n is 1 can be also produced from compound (5) which is obtained by treating compound (3) with an oxidizing agent to obtain a ketone compound, conducting Mannich reaction with iminium salt is a solvent such as hydrogen chloride-methanol, and reacting with alkyllithium ($R^{1D}$—Li).

Method (5): Compounds of Group F

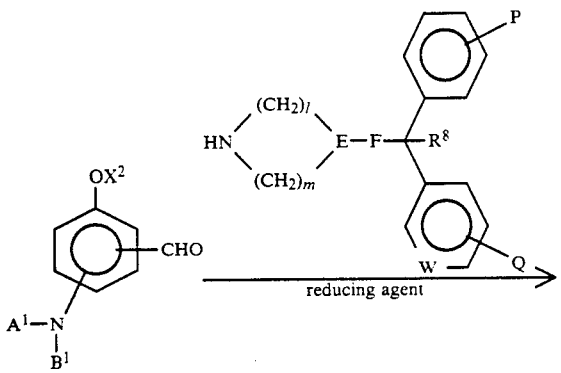

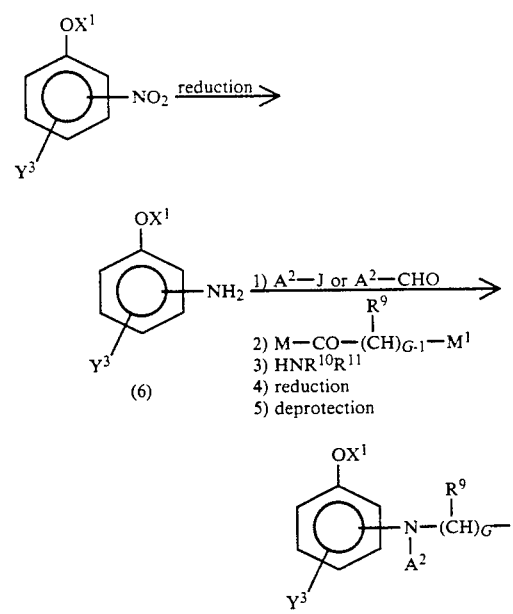

wherein $X^2$ is hydrogen atom, and other symbols are as defined above.

Of the compounds of Group F, a compound wherein t is 1 can be obtained by reacting with amine in a solvent such as methanol at room temperature for 10 minutes to 6 hours, and reduction by a reducing agent such as sodium borohydride.

A compound wherein t is 2–5 can be produced by extending carbon chain by a known method.

Method (6): Compounds of Group G wherein J is halogen such as iodine, and other symbols are as defined above.

First, nitro group is reduced to give an amino compound (6).

In the case of phenyl or pyridyl wherein $A^2$ may be substituted, for example, the amine compound (6) and a halide of $A^2$ ($A^2$—J) is subjected to a coupling reaction in a solvent such as toluene using a copper catalyst for 10 to 100 hours while refluxing.

In the case of benzyl or pyridylmethyl wherein $A^2$ may be substituted, for example, the amine compound (6) and a carbonyl compound ($A^2$—CHO) are reacted as in Method (3), and reduced by a reducing agent.

As mentioned above, after an amine compound is produced, it is reacted with amine ($HNR^{10}R^{11}$), followed by reduction of carbonyl group, and deprotection of phenolic hydroxy, to give a compound of Group G.

Method (7): Compounds of Group H

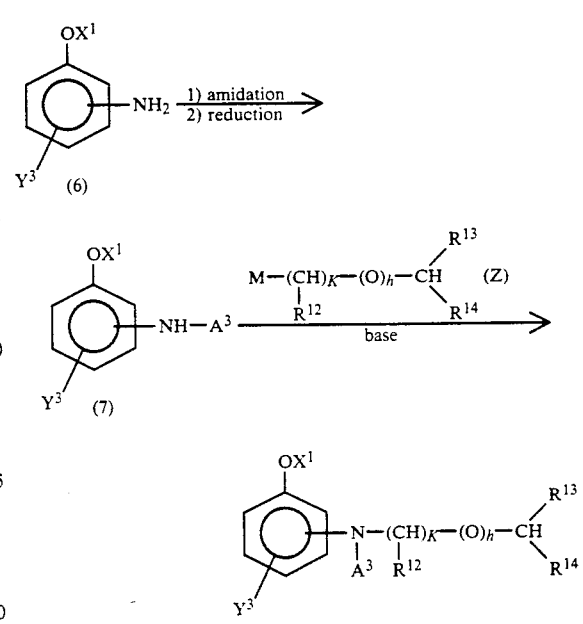

wherein each symbol is as defined above.

Compound (6) is subjected to amidation (e.g. reaction of acid anhydride and amine under anhydrous conditions at 0° C.-room temperature for 1 to 5 hours), after which it is subjected to reduction as mentioned above to give a compound (7).

By the reduction of compound (7) and a base such as butyllithium, and then compound Z, a compound of Group H can be produced.

Said reaction is normally carried out by reacting compound (7) with a base under anhydrous conditions and ice-cooling for 10 minutes to 3 hours, after which reacting with compound Z at room temperature for 1 hour to 1 day.

Method (8): Compounds of Group I

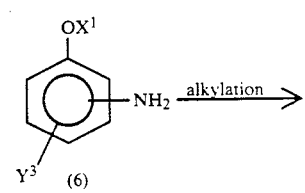

-continued

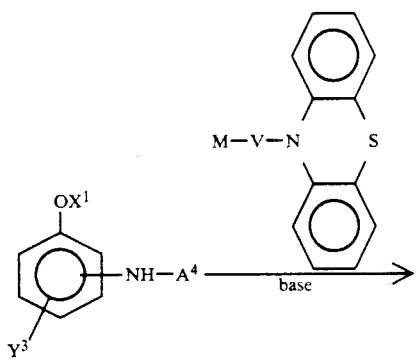

wherein each symbol is as defined above.

Compounds of Group I can be produced according to Method (7).

Method (9): Compounds of Group J

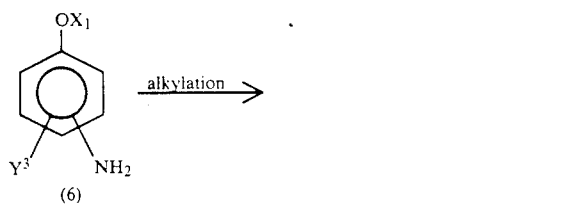

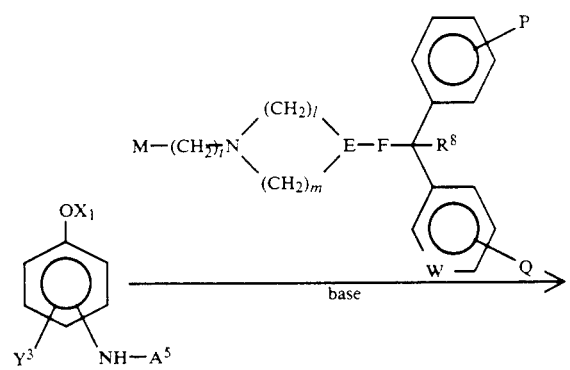

wherein each symbol is as defined above.

Compounds of Group J can be produced according to Method (7).

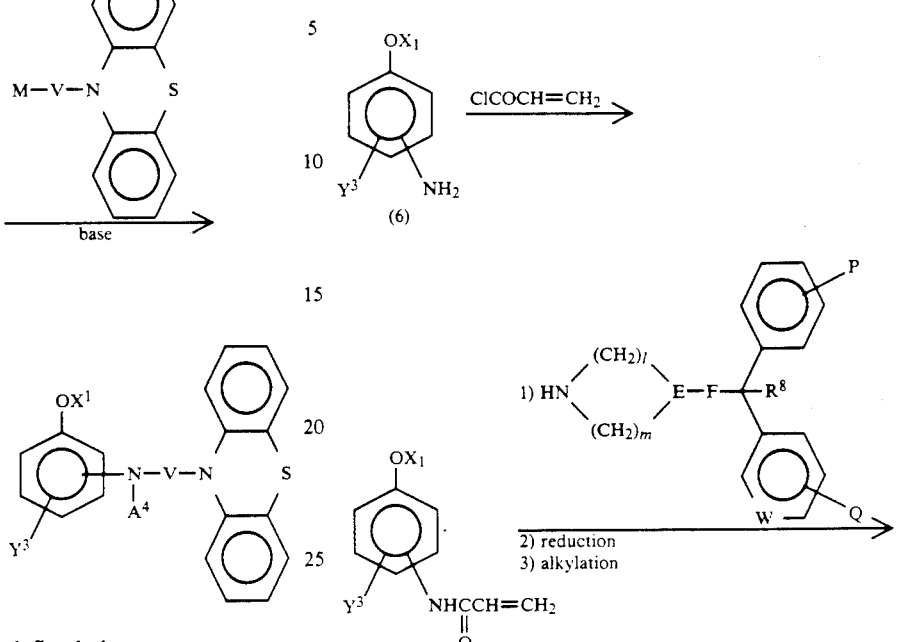

wherein each symbol is as defined above.

Of the compounds of Group J, a compound wherein t is 3 can be produced by, for example, addition by a Michael reaction, and reduction.

The Michael reaction is carried out in a solvent such as ethanol while refluxing for 1 to 5 hours. The reduction of carbonyl and alkylation to follow are as described above.

The novel aminophenol derivative (I) thus produced can be obtained at a desired purity by employing known separation and purification methods such as concentration, extraction, chromatography, reprecipitation, and recrystallization as appropriate.

The starting compound (2) useful for producing the aminophenol derivative (I) of the present invention can be produced by various methods, which are shown in the following reaction scheme.

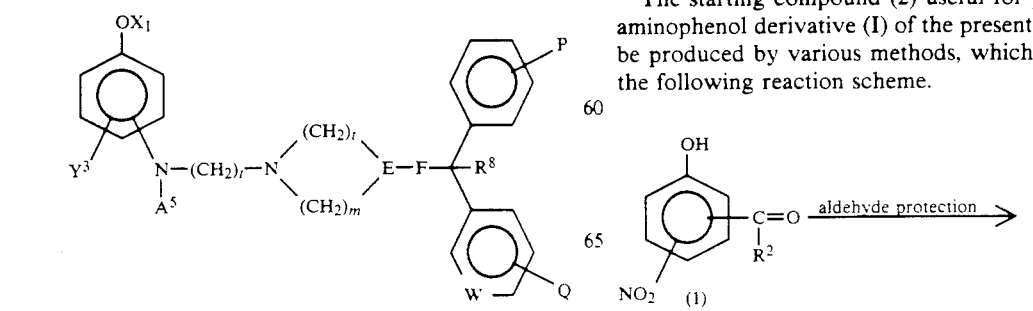

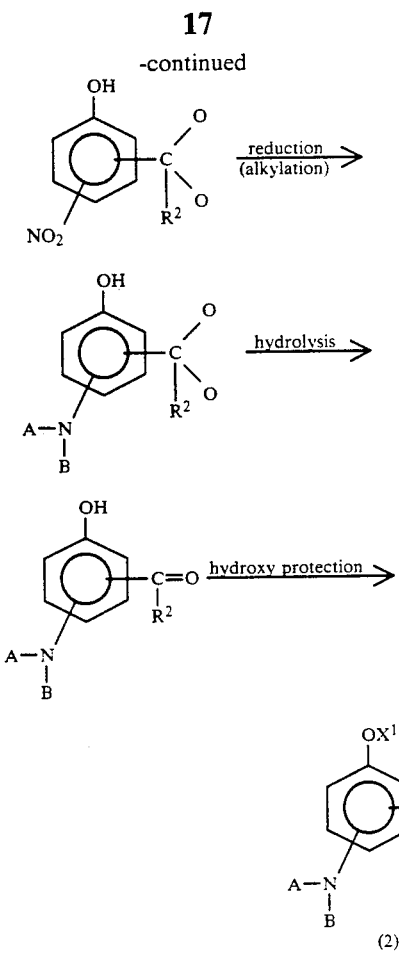

wherein each symbol is as defined above.

First, a compound (1) is subjected to acetalization by heating the compound (1) with an acetalizing agent such as ethylene glycol in the presence of an acid such as p-toluenesulfonic acid in a catalyst amount.

The acetal compound obtained is subjected to reduction, after which it is hydrogenated in the presence of a metal catalyst such as palladium and nickel, to convert nitro group to amino group.

When A and B are lower alkyls, a compound (2) can be produced by alkylation by an alkylating agent such as alkyllithium, or by reductive alkylation, followed by hydrolysis, deprotecting of aldehyde, and protection of phenolic hydroxy by methoxymethyl.

The aminophenol derivative (I) and its pharmacologically acceptable salt of the present invention are extremely low toxic to mammals such as mice, rats, rabbits, dogs, cats, humans, etc.), and markedly suppress generation of active oxygens, and trap them (antioxidative action), and have antiinflammatory and antiallergic actions. Therefore, said compounds are useful for the treatment of diseases caused by excessive production of active oxygens, such as autoimmune diseases, inflammatory diseases, circulatory diseases, and gastrointestinal diseases, and are also useful as antiinflammatory and antiallergic drugs.

When using the aminophenol derivative (I) or its pharmacologically acceptable salt of the present invention as a pharmaceutical as mentioned above, it is administered orally or parenterally as a pharmaceutical composition in the form of powders, granules, tablets, capsules, injections, ointments, skin creams, and so on in an admixture with components necessary for the formulation of the preparations, such as pharmacologically acceptable additives (e.g. carrier, excipient, diluent, etc.). The aminophenol derivative (I) or its pharmacologically acceptable salt is contained in an effective amount. While the dose varies depending on the administration routes, symptoms, body weight and age of patients, and so on, it is desirably 0.05-20 mg/kg body weight/day, particularly 0.1-4 mg/kg body weight/day for an adult orally in a single or several times-divided doses.

The present invention is detailedly described in the following by illustrating Examples, but the present invention is not limited to them.

SYNTHESIS OF COMPOUND A

Synthesis of 4-hydroxy-3-nitrobenzaldehyde ethylene acetal (1)

A solution of 4-hydroxy-3-nitrobenzaldehyde (known compound, 20.6 g, 124 mmol), benzene (150 ml), ethylene glycol (10.3 ml, 185 mmol) and p-toluenesulfonic acid hydrate (catalytic amount) was refluxed overnight removing the resulting water by azeotropic distillation with benzene.

After cooling, the solution was diluted with ethyl acetate, washed with a saturated aqueous solution of sodium hydrogencarbonate and saturated brine, dried over anhydrous magnesium sulfate and evaporated. The thus-obtained solid was recrystallized from ethyl acetate-hexane to give the above-mentioned compound (1). Yield 20.4 g (78%).

Synthesis of 3-dimethylamino-4-hydroxybenzaldehyde ethylene acetal (2)

A solution of the compound (1) (2.00 g, 9.47 mmol) obtained above and 10% palladium-carbon (283 mg, 0.26 mmol) in methanol (70 ml) was stirred under hydrogen atmosphere at room temperature for 2 hours, and thereto was added dropwise 37% formalin (3 ml). The reaction mixture was further stirred under hydrogen atmosphere at room temperature for 14 hours. After completion of the reaction, the palladium-carbon was filtered off, and the filtrate was concentrated. The concentrate was purified by column chromatography on silica gel to give the title dimethylamino compound (2) in a liquid form. Yield 1.23 g (62%).

Synthesis of 3-dimethylamino-4-hydroxybenzaldehyde (3)

A solution of the compound (2) (1.20 g, 5.74 mmol) obtained above in tetrahydrofuran (25 ml) and 1N hydrochloric acid (15 ml) was stirred at 80° C. for 2 hours. After being cooled, the mixture was slowly poured into a saturated aqueous solution of sodium hydrogencarbonate and extracted with ethyl acetate. The extract was washed with saturated brine and dried over anhydrous magnesium sulfate. The solution was concentrated and used for the next reaction without purification.

Synthesis of 3-dimethylamino-4-methoxymethoxybenzaldehyde (Compound A)

To a suspension of sodium hydride (60% in oil, 1.90 g, 47.5 mmol) in dry DMF (60 ml) was added dropwise a solution of the compound (3) (5.98 g, 36.2 mmol) obtained above in DMF (40 ml) under nitrogen atmosphere under ice-cooling. The mixture was stirred at 0° C. for 30 minutes, and thereto was added dropwise chloromethyl methyl ether (3.6 ml, 47.4 mmol). The reaction mixture was stirred at 0° C.-room temperature for 2 hours. The reaction mixture was poured into water, extracted with ethyl acetate, washed with saturated brine, dried over anhydrous magnesium sulfate and evaporated. The concentrate was purified by column chromatography on silica gel to give the title aldehyde compound (Compound A) as yellow liquid. Yield 7.17 g (95%).

IR (neat): 2930, 2810, 2770, 1682, 1585, 1499, 1453, 1419, 1386, 1320, 1233, 1183, 1144, 1109, 1076, 980, 814, 768, 707 cm$^{-1}$ $^1$H-NMR (CDCl$_3$): δ2.85 (s, 6H), 3.54 (s, 3H), 5.34 (s, 2H), 7.24 (d, 2H, J=8.1 Hz), 7.44–7.49 (m, 2H), 9.87 (s, 1H)

EXAMPLE 1

Synthesis of
1-(4-chlorophenyl)-1-(3-dimethylamino-4-methoxymethoxyphenyl)methanol (1)

To a solution of p-bromochlorobenzene (2.40 g, 12.5 mmol) in anhydrous tetrahydrofuran (12.5 ml) was added dropwise n-butyl lithium (1.6M, 7.84 ml, 12.5 mmol) under nitrogen atmosphere at −78° C., and the mixture was stirred for 20 minutes. A solution of compound A (2.20 g, 11.9 mmol) in anhydrous tetrahydrofuran (12.5 ml) was added dropwise thereto at the same temperature, and the mixture was further stirred at room temperature for 1 hour. The reaction mixture was poured into a saturated aqueous solution of ammonium chloride, extracted with ethyl acetate, washed with water and saturated brine and dried over anhydrous magnesium sulfate. The solvent was distilled off, and the residue was crystallized from ethyl acetate-hexane (yield 1.46 g). The mother liquor was further purified by column chromatography on silica gel to give the title compound (1). Yield 2.29 g (59%).

Synthesis of
2-[1-(4-chlorophenyl)-1-(3-dimethylamino-4-methoxymethoxyphenyl)methoxy]-N,N-dimethylethanamine (2)

A solution of the compound (1) (1.37 g, 4.26 mmol), 2-(dimethylamino)ethylchloride hydrochloride (1.84 g, 12.3 mmol) and tetrabutylammonium hydrogensulfate (145 mg, 0.43 mmol) in methylene chloride (8.5 ml) and 4N sodium hydroxide (8.5 ml) was stirred under nitrogen atmosphere at room temperature for about 60 hours. The reaction mixture was diluted with water, extracted with methylene chloride, dried over anhydrous magnesium sulfate and evaporated. The residue was purified by column chromatography on silica gel to recover the compound (1) (60% recovery) and to give the title compound (2). Yield 0.45 g (30%).

Synthesis of
2-[1-(4-chlorophenyl)-1-(3-dimethylamino-4-hydroxyphenyl)methoxy]-N,N-dimethylethanamine (Compound 1)

A solution of the compound (2) (0.43 g, 1.09 mmol) obtained above in 1N hydrochloric acid (3.28 ml) and tetrahydrofuran (2 ml) was heated under reflux for 3 hours. Thereto was added additional 1N hydrochloric acid (2.18 ml) and the mixture was further heated for 1.5 hours. The reaction mixture was poured into a saturated aqueous solution of sodium hydrogencarbonate, extracted with methylene chloride, dried over anhydrous magnesium sulfate and evaporated. The residue was purified by column chromatography on silica gel to give the title compound (Compound 1). Yield 0.15 g (39%).

IR (neat): 2900, 2800, 2720, 1590, 1500 cm$^{-1}$ $^1$H-NMR (DMSO-d$_6$): δ2.15 (s, 6H), 2.46 (t, 2H, J=5.8 Hz), 2.64 (s, 6H), 3.43 (t, 2H, J=5.8 Hz), 5.31 (s, 1H), 6.70 (s, 2H), 6.83 (s, 1H), 7.35 (s, 4H)

EXAMPLE 2

Synthesis of
1-(3-dimethylamino-4-methoxymethoxyphenyl)-1-(2-pyridyl)methanol (1)

To a solution of 2-bromopyridine (3.05 g, 19.3 mmol) in dry tetrahydrofuran (100 ml) was added dropwise n-butyl lithium in hexane (1.6M, 12.0 ml, 19.2 mmol) under nitrogen atmosphere. After stirring at −78° C. for 30 minutes, thereto was added dropwise a solution of the aldehyde compound (Compound A) (3.00 g, 14.3 mmol) in dry tetrahydrofuran (20 ml), and the mixture was stirred at −78° C. for 2 hours. A saturated aqueous solution of ammonium chloride (10 ml) was added thereto, and the mixture was stirred at room temperature for 50 minutes. The reaction mixture was poured into a saturated aqueous solution of ammonium chloride (200 ml) and extracted with ethyl acetate.

The extract was washed with saturated brine, dried over anhydrous magnesium sulfate and evaporated. The concentrate was purified by column chromatography on silica gel to give the alcohol compound (1) as yellow liquid. Yield 4.09 g (99%).

Synthesis of
2-[1-(3-dimethylamino-4-methoxymethoxyphenyl)-1-(2-pyridyl)methoxy]-N,N-dimethylethanamine (2)

A mixture of the alcohol compound (1) (2.74 g, 9.50 mmol) obtained above, methylene chloride (40 ml), 2-(dimethylamino) ethyl chloride hydrochloride (2.77 g, 19.2 mmol), tetra-n-butylammonium hydrogensulfate (351 mg, 1.03 mmol) and a 30% aqueous solution of sodium hydroxide (35 ml) was stirred at room temperature for 18 hours. The reaction mixture was poured into water and extracted with methylene chloride. The extraxt was washed with saturated brine, dried over anhydrous magnesium sulfate and evaporated. The concentrate was purified by column chromatography on silica gel to give the dimethylamino compound (2) as a yellow oil. Yield 1.83 g (54%).

Synthesis of
2-[1-(3-dimethylamino-4-hydroxyphenyl)-1-(2-pyridyl)methoxy]-N,N-dimethylethanamine (Compound 2)

A solution of the dimethylamino compound (2) (1.86 g, 5.17 mmol) obtained above in tetrahydrofuran (30 ml) and 1hydrochloric acid (30 ml) was heated at 80° C. and stirred for 3 hours. The reaction mixture was added to cooled 1N sodium hydroxide (60 ml) and extracted with ethyl acetate. The organic layer was washed with brine, dried over anhydrous magnesium sulfate and evaporated. The concentrate was purified by column chromatography on silica gel to give the aminophenol compound (Compound 2) as a yellow oil. Yield 1.07 g (66%).

IR (neat): 3150, 2920, 2840, 2800, 2770, 1592, 1500, 1451, 1432, 1308, 1235, 1191, 1102, 1048, 975, 878, 808, 753, 670 cm$^{-1}$ $^1$H-NMR (DMSO-d$_6$): δ2.16 (s, 6H), 2.49 (t, 2H, J=5.8 Hz), 2.64 (s, 6H), 3.25-3.75 (m, 3H), 5.33 (s, 1H), 6.70 (d, 1H, J=8.1 Hz), 6.77 (dd, 1H, J=1.6, 8.1 Hz), 6.89 (d, 1H, J=1.6 Hz), 7.21 (dd, 1H, J=0.8, 5.8 Hz), 7.52 (d, 1H, J=7.8 Hz), 7.76 (dt, 1H, J=1.6, 7.7 Hz), 8.45 (d, 1H, J=4.0 Hz)

EXAMPLE 3

Synthesis of 5-[1-(4-chlorophenyl)-1-(4-methylpiperazino)]methyl-N,N-dimethyl-2-methoxymethoxyaniline (1)

To a solution of N-chlorosuccinimide (622 mg, 4.66 mmol) in methylene chloride (20 ml) was added dropwise methyl sulfide (0.41 ml, 5.59 mmol) under nitrogen atmosphere while stirring under ice-cooling. The reaction mixture was then cooled in the 4%mperature range of −25° C. to −20° C., and thereto was added dropwise a solution of 1-(4-chlorophenyl)-1-(3-dimethylamino-4-methoxymethoxyphenyl)methanol (1.00 g, 3.11 mmol) in methylene chloride (4 ml). The mixture was again cooled on a ice bath and stirred for 2 hours. N-methylpiperazine (0.76 ml, 6.48 mmol) was added dropwise thereto. The mixture was stirred at room temperature for 16 hours and evaporated under reduced pressure. A saturated aqueous solution of sodium hydrogencarbonate was added to the residue, and the mixture was extracted with ethyl acetate. The ethyl acetate layer was washed with water, a saturated aqueous solution of sodium hydrogencarbonate and saturated brine, dried over anhydrous magnesium sulfate and evaporated. The residue was purified by column chromatography on silica gel to give the title compound (1) (1.58 g) in quantative yield.

Synthesis of 4-[1-(4-chlorophenyl)-1-(4-methylpiperazino)]methyl-2-dimethylaminophenol (Compound 3)

To a solution of the compound (1) (1.22 g, 3.02 mmol) obtained above in methylene chloride (20 ml) was added thiophenol (0.37 ml, 3.62 mmol) and boron trifluoride-ether complex salt (2.4 ml, 19.5 mmol) under nitrogen atmosphere at room temperature, and the mixture was stirred for 3 hours. The reaction mixture was poured into a saturated aqueous solution of sodium hydrogencarbonate under ice-cooling and extracted with ethyl acetate. The ethyl acetate layer was washed with a saturated aqueous solution of sodium hydrogencarbonate and extracted with 0.2hydrochloric acid. The combined water layer was washed with ethyl acetate. The water layer was poured into a saturated aqueous solution of sodium hydrogencarbonate and the pH of the solution was made basic. After the extraction with ethyl acetate, the extract was washed with a saturated aqueous solution of sodium hydrogencarbonate and saturated brine, dried over anhydrous magnesium sulfate and evaporated. The residue was purified by column chromatography on silica gel to give Compound 3 as an orange amorphous. Yield 584 mg (54%).

IR (KBr): 3600-3200, 2930, 2780, 1590, 1500, 1485, 1450, 1290, 1240, 1140, 1090, 1005 cm$^{-1}$ $^1$H-NMR (DMSO-d$_6$): δ2.12 (s, 3H), 2.28 (m, 8H), 2.62 (s, 6H), 4.09 (s, 1H), 6.63 (d, 1H, J=8.1 Hz), 6.74 (dd, 1H, J=1.7, 8.1 Hz), 6.83 (d, 1H, J=1.7 Hz), 7.27 (d, 2H, J=8.5 Hz), 7.38 (d, 2H, J=8.5 Hz)

EXAMPLE 4

Synthesis of N-(3-dimethylamino-4-methoxymethoxybenzyl)aniline (1)

To a solution of Compound A (1.71 g, 8.17 mmol) in methanol (80 ml) was added dropwise aniline (1.49 ml, 16.3 mmol), and the mixture was stirred at room temperature for 15 minutes. Thereto was added sodium cyanoborohydride (1.62 g, 24.5 mmol) by portions. The pH of the reaction mixture was adjusted to 7 by the addition of hydrochloric acid-methanol. After being stirred for 1 hour, the reaction mixture was poured into water and basified with sodium hydrogencarbonate. The mixture was extracted with ethyl acetate, washed with water, a saturated aqueous solution of sodium hydrogencarbonate and saturated brine, dried over anhydrous magnesium sulfate and evaporated to give the title compound (1) (2.82 g) in quantative yield.

Synthesis of N-chloroacetyl-N-(3-dimethylamino-4-methoxymethoxybenzyl)aniline (2)

A mixture of the compound (1) (2.80 g) obtained above, benzene (9 ml), ether (3 ml), water (3 ml), ice (12 g) and potassium carbonate (1.13 g, 8.17 mmol) was stirred under ice-cooling for 30 minutes, and thereto was added dropwise chloroacetyl chloride (0.98 ml, 12.3 mmol). After being stirred at room temperature for 1 hour, the reaction mixture was extracted with ethyl acetate, washed with water, a saturated aqueous solution of sodium hydrogencarbonate and saturated brine, dried over anhydrous magnesium sulfate and evaporated. The residue was purified by column chromatography on silica gel to give the compound (2) (1.73 g) in 57% yield from 3-dimethylamino-4-methoxymethoxybenzaldehyde.

Synthesis of N-dimethylaminoacetyl-N-(3-dimethylamino-4-methoxymethoxybenzyl)aniline (3)

To the compound (2) (1.68 g, 4.63 mmol) obtained above was added a 50% aqueous solution of dimethylamine (8 ml) under ice-cooling. After being stirred at room temperature for 1.5 hours, the reaction mixture was extracted with ethyl acetate. The ethyl acetate layer was washed with water and saturated brine, dried over anhydrous magnesium sulfate and evaporated. The residue was purified by column chromatography on silica gel to give the object compound (3). Yield 1.57 g (91%).

Synthesis of 2-dimethylamino-4-[N-(2-dimethylaminoethyl)-N-phenyl]aminomethylphenol (Compound 4)

To a solution of the compound (3) (1.54 g, 4.15 mmol) obtained above in water (100 ml) was added 3N hydrochloric acid, and the mixture was heated and stirred at 65° C. for 1 hour. The reaction mixture was neutralized with sodium hydrogen-carbonate under ice-cooling and extracted with ethyl acetate. The extract was washed with a saturated aqueous solution of sodium hydrogencarbonate and saturated brine, dried over anhydrous magnesium sulfate and evaporated. The residue was purified by column chromatography on silica gel to give the deprotective derivative of the compound (3) (1.10 g). To a solution of thus obtained compound in dry tetrahydrofran was added dropwise boran-methyl sulfide (1.5 ml) under ice-cooling while stirring. The mixture was stirred overnight while being heated at 80° C. The reaction mixture was cooled on a ice bath, and hydrogen chloride-methanol was added thereto. The mixture was again heated at 80° C. for 1 hour and evaporated, and ether was poured upon the residue. After the ether was distilled off, thus obtained residue was dissolved in water and neutralized with sodium hydrogencarbonate under ice-cooling. The mixture was extracted with ethyl acetate, washed with a saturated aqueous solution of sodium hydrogencarbonate and saturated brine, dried over anhydrous magnesium sulfate and evaporated. The residue was purified by column chromatography on silica gel and recrystallized from ethyl acetate-hexane to give Compound 4.

Yield 241 mg (23%). m.p. 124.0°–125.0° C.

IR (KBr): 2340, 1595, 1505, 1450, 1395, 1235, 1165, 1155, 740 cm$^{-1}$ $^1$H-NMR (DMSO-d$_6$): δ2.53 (s, 6H), 2.62 (s, 6H), 2.84 (t, 2H, J=7.9 Hz), 3.75 (t, 2H, J=7.9 Hz), 4.38 (s, 2H), 6.55–6.74 (m, 6H), 7.08–7.16 (m, 2H)

EXAMPLE 5

Synthesis of 4'-hydroxy-3'-nitroacetophenone ethylene acetal (1)

A solution of 4'-hydroxy-3'-nitroacetophenone (known compound, 12.1 g, 67.0 mmol), benzene (100 ml), ethylene glycol (5.61 ml, 100 mmol) and p-toluenesulfonic acid hydrate (catalytic amount) was refluxed overnight removing the resulting water by azeotropic distillation with benzene. To the reaction mixture was added a saturated aqueous solution of sodium hydrogencarbonate, and the mixture was extracted with ethyl acetate, washed with saturated brine, dried over anhydrous magnesium sulfate and evaporated. The residue was purified by column chromatography on silica gel to give the object compound (1) as an oil. Yield 14.6 g (97%).

Synthesis of 3'-dimethylamino-4'-hydroxyacetophenone ethylene acetal (2)

A solution of the compound (1) (14.6 g, 64.8 mmol) obtained above and 10% palladium-carbon (1.30 g, 1.30 mmol) in methanol (64 ml) was stirred under hydrogen atmosphere at room temperature for 2 hours. Then thereto was added dropwise 37% formalin (8.99 ml, 324 mmol), and the reaction mixture was further hydrogenated overnight. The palladium-carbon was filtered off, and the solvent was distilled off. The residue was purified by column chromatography on silica gel, and thus obtained solid was further washed with hexane and filtered to give the object compound (2). Yield 4.73 g (33%).

Synthesis of 3'-dimethylamino-4'-hydroxyacetophenone (3)

A solution of the compound (2) (4.73 g, 21.2 mmol) obtained above in tetrahydrofuran (20 ml) and 1N hydrochloric acid (63.5 ml) was heated and stirred for 1.5 hours. The mixture was poured into a saturated aqueous solution of sodium hydrogencarbonate, extracted with ethyl acetate, washed with saturated brine and dried over anhydrous magnesium sulfate. The solvent was distilled off, and the residual solid was washed with hexane and filtrated. Yield 3.46 g (91%).

Synthesis of 3-dimethylamino-1-(3-dimethylamino-4-hydroxyphenyl)-1-propanone (4)

A solution of the compound (3) (1.71 g, 9.54 mmol) obtained above, dimethylmethyleneammonium chloride (0.98 g, 10.5 mmol) and hydrogen chloride-methanol reagent (20 ml) was heated and stirred overnight. After the solvent was distilled off, a saturated aqueous solution of sodium hydrogencarbonate was added to the residue. The mixture was extracted with chloroform, dried over anhydrous magnesium sulfate and evaporated. The residue was purified by column chromatography on silica gel to give the object compound (4). Yield 1.53 g (68%).

Synthesis of 2-dimethylamino-4-[1-(4-chlorophenyl)-3-dimethylamino-1-hydroxypropyl]phenol (5)

To a solution of p-bromochlorobenzene (4.93 g, 25.7 mmol) in anhydrous tetrahydrofuran (25 ml) was added dropwise butyl lithium (1.6M, 16.1 ml, 25.7 mmol) under nitrogen atmosphere at −78° C., and the mixture was stirred at the same temperature for 30 minutes. A solution of the compound (4) (1.52 g, 6.43 mmol) obtained above in anhydrous tetrahydrofuran was added thereto, and the mixture was stirred at room temperature for 2 hours. The reaction mixture was poured into a saturated aqueous solution of ammonium chloride, extracted with chloroform, washed with saturated brine and dried over anhydrous magnesium sulfate. The solvent was distilled off, and the residue was purified by column chromatography on silica gel to give the object compound (5). Yield 1.90 g (85%).

Synthesis of 1-(4-chlorophenyl)-3-dimethylamino-1-(3-dimethylamine-4-hydroxyphenyl)-1-propene (Compound 5)

A solution of the compound (5) (1.90 g, 5.45 mmol) obtained above in 65% sulfuric acid (10 ml) was stirred at 160° C. for 30 minutes. The reaction mixture was poured into an aqueous solution of sodium hydrogencarbonate, diluted with water, extracted with chloroform and dried over anhydrous magnesium sulfate. The solvent was distilled off, and the residue was purified by column chromatography on silica gel to give Compound 5. Yield 1.70 g (94%).

IR (CHCl$_3$): 3300, 3000–2750, 1590, 1500 cm$^{-1}$ $^1$H-NMR (DMSO-d$_6$): δ2.10 (s, 6H), 2.13 (s, 3H), 2.63 (s, 3H), 2.65 (s, 3H), 2.83 (t, 1H, J=6.8 Hz), 2.93 (d, 1H, J=6.7 Hz), 6.01 (t, 0.5H, J=6.8 Hz), 6.04 (t, 0.5H, J=6.7 Hz), 6.50–6.81 (m, 3H), 7.12–7.46 (m, 4H)

EXAMPLE 6

Synthesis of 4-[1-(4-chlorophenyl)-3-dimethylaminopropyl]-2-dimethylaminophenol (Compound 6)

A solution of Compound 5 (1.14 g, 3.45 mmol) obtained above and platinum oxide (39 mg, 0.17 mmol) in ethanol (20 ml) was stirred under hydrogen atmosphere at room temperature for 6 hours. The platinum was filtered off, and the mother liquor was evaporated. The residue was purified by column chromatography on silica gel to give Compound 6. Yield 374 mg (25%).

IR (neat): 3300, 3000–2700, 1595, 1500 cm$^{-1}$ $^1$H-NMR (DMSO-d$_6$): δ2.0–2.1 (m, 4H), 2.08 (s, 6H), 2.63 (s, 6H), 3.87 (bs, 1H), 6.67 (s, 2H), 6.74 (s, 1H), 7.29 (s, 4H)

EXAMPLE 7

Synthesis of 4-[4-(4-chlorobenzhydryl)piperazino]methyl-2-dimethylaminophenol (Compound 7)

To a solution of 3-dimethylamino-4-hydroxybenzaldehyde (see Synthesis of Compound A) (600 mg, 3.63 mmol) in methanol (10 ml) was added 1-(4-chlorobenzhydryl)piperazine (1.25 g, 4.36 mmol) while stirring at room temperature. Thereto was added sodium cianoborohydride (95% content) (700 mg, 10.6 mmol) by portions. After stirring for 1 hour, acetic acid (0.2 ml) was added thereto, and the mixture was further stirred for 3 hours. The reaction mixture was poured into water, and the pH of the solution was made basic by the addition of a saturated aqueous solution of sodium hydrogencarbonate. The solution was extracted with ethyl acetate and washed with a saturated aqueous solution of sodium hydrogencarbonate. The extract was then extracted with 1N hydrochloric acid, and the aqueous layer was neutralized and extracted with ethyl acetate. Then thus obtained extract was washed with a saturated aqueous solution of sodium hydrogencarbonate and saturated brine, dried over anhydrous magnesium sulfate and evaporated. The residue was purified by column chromatography on silica gel to give the object Compound 7. Yield 569 mg (36%).

IR (CHCl$_3$): 3000, 2800, 1500, 1200, 710, 660 cm$^{-1}$
$^1$H-NMR (DMSO-d$_6$): δ2.20–2.50 (br, 8H), 2.64 (s, 6H), 3.33 (s, 2H), 4.28 (s, 1H), 6.67 (s, 2H), 6.75 (s, 1H), 7.14–7.46 (m, 9H)

EXAMPLE 8

Synthesis of 1-methoxymethoxy-4-methyl-2-nitrobenzene (1)

To a suspension of sodium hydride (60% in oil, 4.78 g, 0.12 mol) in dry DMF (100 ml) was added dropwise a solution of 4-methyl-2-nitrophenol (known compound) (15.6 g, 0.102 mol) in DMF (50 ml) under nitrogen atmosphere under ice-cooling over a period of 30 minutes. The mixture was stirred at 0° C. for 30 minutes, and thereto was added dropwise chloromethyl methyl ether (9.3 ml, 0.122 mol). The reacion mixture was stirred at 0° C. for 1 hour. The reaction mixture was poured into water and extracted with ethyl acetate. The organic layer was washed with saturated brine, dried over anhydrous magnesium sulfate and evaporated. The concentrate was purified by column chromatography to give the ether compound (1). Yield 20.1 g (100%).

Synthesis of 2-methoxymethoxy-5-methylaniline (2)

A solution of the nitro compound (1) (20.0 g, 0.101 mol) obtained above and 10% palladium-carbon (1.55 g, 146 mmol) in ethyl acetate (250 ml) was stirred under hydrogen atmosphere at room temperature for 3 hours. Then the palladium-carbon was filtered off, and the solvent was distilled off from the mother liquor. The crude product was purified by column chromatography to give the aniline compound (2). Yield 16.6 g (98%).

Synthesis of 2-methoxymethoxy-5-methyl-N-phenylaniline (3)

A mixture of 2-methoxymethoxy-5-methylaniline (10.1 g, 60.4 mmol) obtained above, toluene (150 ml), iodobenzene (10.0 ml, 89.4 mmol), activated copper powder (2.01 g, 31.8 mmol), copper(I) iodide (611 mg, 3.21 mmol) and potassium carbonate (6.93 g, 50.1 mmol) was refluxed for 67 hours. After being cooled, the reaction mixture was poured into water and extracted with ethyl acetate. The organic layer was washed with saturated brine, dried over anhydrous magnesium sulfate and evaporated. The concentrate was purified by column chromatography on silica gel to give the object N-phenylaniline derivative as a mixture with N,N-diphenylaniline derivative (1:1, 3.17 g).

Synthesis of N-chloroacetyl-2-methoxymethoxy-5-methyl-N-phenylaniline (4)

To a solution of the N-phenylaniline (3) obtained above (a mixture with dibenzyl derivative in the ratio of 1:1, 3.17 g), benzene (40 ml), water (40 ml) and potassium carbonate (1.64 g, 11.7 mmol) was added dropwise chloroacetyl chloride (1.0 ml, 12.6 mmol) under ice-cooling. After being stirred at 0° C.-room temperature for 4 hours, chloroacetyl chloride (0.5 ml, 6.3 mmol) was added dropwise again. Four hours later, chloroacetyl chloride (0.5 ml, 6.3 mmol) was further added. After being stirred at room temperature for 15 hours, the reaction mixture was poured into water and extracted with ethyl acetate. The organic layer was washed with brine, dried over anhydrous magnesium sulfate and evaporated. The crude product was purified by column chromatography on silica gel to give the amide compound (4) as a mixture, which was immediately used for the next reaction.

Synthesis of N-dimethylaminoacetyl-2-methoxymethoxy-5-methyl-N-phenylaniline (5)

To the mixture of the α-chloroamide compound (4) obtained above was added a dimethylamine solution (50% abt, 30 ml) under ice-cooling. After being stirred at 0° C. to room temperature for 1 hour, the reaction mixture was extracted with ethyl acetate. The extract was washed with saturated brine, dried over anhydrous magnesium sulfate and evaporated. The crude product was purified by column chromatography on silica gel to give the amide compound (5) as a colorless oil. Yield 1.04 g (5.2% from the aniline compound).

Synthesis of N,N-dimethyl-N'-(2-hydroxy-5-methylphenyl)-N'-phenylethylenediamine (Compound 8)

To a solution of the amide compound (5) (1.00 g, 3.04 mmol) obtained above in dry tetrahydrofran (10 ml) was added dropwise borane-methyl sulfide (10.0–10.2M, 0.9 ml, 9 mmol) under ice-cooling. The mixture was stirred at 0° C. for 1 hour, at room temperature for 30 minutes and then at 70° C. for 15 hours. The reaction mixture was again cooled with a ice bath, and thereto was added dropwise water (2 ml) and 1N hydrochloric acid (10 ml). The mixture was stirred at 70° C. for 4 hours. The reaction mixture was poured into cooled 1N sodium hydroxide (20 ml) and extracted with ethyl acetate. The organic layer was washed with brine, dried over anhydrous magnesium sulfate and evaporated. The concentrate was purified by column chromatography on silica gel to give yellow crystals. The thus obtained crystals were recrystallized from chloroform-hexane (1:1) 4o give the object aminophenol compound (Compound 8) as white crystals. Yield 436 mg (53%). m.p. 88.5°–89.5° C.

IR (KBr): 2950, 2850, 2810, 2560, 1597, 1492, 1333, 1286, 1242, 1182, 1163, 1126, 1034, 951, 822, 803, 755, 695, 515 cm$^{-1}$ $^1$H-NMR (DMSO-d$_6$): δ2.16 (s, 3H), 2.18 (s, 6H), 2.54 (t, 2H, J=5.5 Hz), 3.65 (t, 2H, J=5.4 Hz), 6.46 (d, 2H, J=8.3 Hz), 6.60 (t, 1H, J=7.2 Hz), 6.78 (s, 1H), 6.83 (d, 1H, J=8.2 Hz), 6.96 (dd, 1H, J=1.7, 8.3 Hz), 7.08 (t, 2H, J=8.1 Hz)

EXAMPLE 9

Synthesis of N-benzyl-2-methoxymethoxy-5-methylaniline (1)

To a solution of 2-methoxymethoxy-5-methylaniline (see Example 8) (15.6 g, 93.3 mmol), ethanol (100 ml), acetic acid (75 ml), benzaldehyde (19.0 ml, 187 mmol) and sodium acetate (15.5 g, 189 mmol) was added sodium borohydride (7.15 g, 189 mmol) under ice-cooling over a period of 30 minutes. The reaction mixture was stirred at 0° C. to room temperature for 1 hour. The reaction mixture was poured into 1sodium hydroxide (500 ml) and extracted with ethyl acetate. The extract was washed with brine, dried over anhydrous magnesium sulfate and evaporated. The crude product was purified by column chromatography on silica gel to give white crystals. The crystals were recrystallized from chloroformohexane to give the desired benzylaniline compound (1). Yield 25.2 g (86%, a mixture with dibenzyl compound in the ratio of 6:1).

Synthesis of N-benzyl-N-chloroacetyl-2-methoxymethoxy-5-methylaniline (2)

To a solution of the benzylaniline compound (1) obtained above (a mixture with dibenzyl compound with a ratio of 6:1, 5.10 g, 16.2 mmol), benzene (60 ml), water (60 ml) and potassium carbonate (2.24 g, 16.2 mmol) was added dropwise chloroacetyl chloride (2.0 ml, 25.1 mmol) under ice-cooling. After being stirred at room temperature for 1 hour, the reaction mixture was poured into a saturated aqueous solution of sodium hydrogen-carbonate and extracted with ethyl acetate. The organic layer was washed with brine, dried over anhydrous magnesium sulfate and evaporated. The crude product was purified by column chromatography on silica gel to give the amide compound (2). Yield 5.17 g (96%).

Synthesis of N-benzyl-N-dimethylaminoacetyl-2-methoxymethoxy-5-methylaniline (3)

To the α-chloroamide compound (2) (5.20 g, 15.6 mmol) obtained above was added a solution of dimethylamine (50% abt., 50 ml) under ice-cooling. After being stirred at 0° C. for 30 minutes, the reaction mixture was extracted with ethyl acetate. The extract was washed with saturated brine, dried over anhydrous magnesium sulfate and evaporated to give the α-aminoamide compound (3) as a colorless oil. Yield 5.31 g (99%).

Synthesis of N-benzyl-N',N'-dimethyl-N-(2-hydroxy-5-methylphenyl)ethylenediamine (Compound 9)

To a solution of the amide compound (3) (5.26 g, 15.4 mmol) obtained above in dry tetrahydrofran (60 ml) was added dropwise borane-methyl sulfide (10.0–10.2M, 4.0 ml, 40 mmol) under nitrogen atmosphere under ice-cooling over a period of 10 minutes. The reaction mixture was stirred at 0° C. for 30 minutes, at room temperature for 1 hour and then at 70° C. for 2 hours. The reaction mixture was again cooled on a ice bath, and thereto was added dropwise water (10 ml) and 1N hydrochloric acid (30 ml). The mixture was stirred at 80° C. for 14 hours. The reaction mixture was poured into a cooled 4N aqueous sodium hydroxide and extracted with ethyl acetate. The organic layer was washed with brine, dried over anhydrous magnesium sulfate and evaporated. The concentrate was purified by column chromatography on silica gel to give the desired aminophenol compound (Compound 9) as white crystals. Yield 930 mg (21%). m.p. 58°–59° C.

IR (KBr): 3400, 3010, 2940, 2840, 2770, 1584, 1500, 1450, 1348, 1266, 1240, 1129, 937, 814, 771, 736, 694 cm$^{-1}$ $^1$H-NMR (DMSO-d$_6$): δ2.11 (s, 3H), 2.15 (s, 6H), 2.23 (t, 2H, J=5.2 Hz), 2.89 (t, 2H, J=5.1 Hz), 3.40 (bs, 1H), 4.19 (s, 2H), 6.59 (d, 1H, J=8.0 Hz), 6.65 (dd, 1H, J=1.6, 8.0 Hz), 6.94 (d, 1H, J=1.4 Hz), 7.12–7.37 (m, 5H)

EXAMPLE 10

Synthesis of 2-formylamino-4-methylphenol (1)

To 2-amino-p-cresol (8.01 g, 65 mmol) was added formic acid (5.98 g, 130 mmol) and the mixture was refluxed for 1 hour. The reaction mixture was allowed to stand for cooling. After the addition of ethyl acetate, the mixture was poured into ice-cold water. The aqueous layer was neutralized with a saturated aqueous solution of sodium hydrogencarbonate and extracted with ethyl acetate. The organic layer was washed with a saturated aqueous solution of sodium hydrogencarbonate and saturated brine, dried over anhydrous magnesium sulfate and evaporated. The residue was purified by column chromatography on silica gel and recrystallized from ethyl acetate-hexane to give the title compound (1). Yield 8.59 g (88%).

Synthesis of 4-methyl-2-methylaminophenol (2)

To a suspension of lithium aluminium hydride (3.56 g, 94 mmol) in dry ether (100 ml) was added dropwise a solution of the compound (1) (10.9 g, 72 mmol) in dry ether (600 ml) under ice-cooling. The mixture was stirred under ice-cooling for 30 minutes, and thereto was added ethyl acetate and water in that order. The aqueous layer was neutralized with diluted hydrochloric acid and extracted with ether. The organic layer was washed with saturated brine, dried over anhydrous magnesium sulfate and evaporated. The residue was purified by column chromatography on silica gel to give the title compound (2). Yield 7.63 g (77%).

Synthesis of 2-bromoethyl benzhydryl ether (3)

To 2-bromoethanol (40.7 g, 326 mmol) was added conc. sulfuric acid (9.96 g, 102 mmol) under ice-cooling while stirring. Thereto was added benzhydrol (12.0 g, 65.1 mmol), and the mixture was heated at 100° C. for 15 minutes. The reaction mixture was allowed to stand for cooling, poured into ice-cold water and extracted with ether. The organic layer was washed with a saturated aqueous solution of sodium hydrogencarbonate and saturated brine, dried over anhydrous magnesium sulfate and evaporated. The thus-obtained liquid was distilled under reduced pressure to give the title compound (3). Yield 13.9 g (73%). b.p. 125°–165° C./2.5 mmHg.

Synthesis of 2-[N-(2-benzhydryloxyethyl-N-methyl]amino-4-methylphenol (Compound 10)

To a solution of the compound (2) (1.00 g, 7.3 mmol) in dry tetrahydrofuran (30 ml) was added dropwise n-butyllithium (c.a. 1.6M, 10.5 ml, 16.8 mmol) under ice-cooling while stirring. After stirring at 0° C. for 45 minutes, HMPA (2.0 ml, 11.5 mmol) was added thereto and the mixture was further stirred at the same temperature for 30 minutes. Thereto was added dropwise the compound (3) (2.33 g, 8.03 mmol) obtained above, and the mixture was further stirred for 1 hour. The reaction mixture was poured into ice-cold water, extracted with ethyl acetate, washed with water and saturated brine, dried over anhydrous magnesium sulfate and evaporated. The residue was purified by column chromatography on silica gel to give crystals. The thus-obtained crystals were recrystallized from ethyl acetate-hexane to give the Compound 10. Yield 1.01 g (33%). m.p. 81.0°–81.5° C.

IR (KBr): 3350, 2850, 1500, 1260, 1090, 1060, 810, 760, 700 cm$^{-1}$ $^1$H-NMR (DMSO-d$_6$): δ2.17 (s, 3H), 2.71 (s, 3H), 3.23 (t, 2H, J=5.5 Hz), 3.50 (t, 2H, J=5.5 Hz), 5.42 (s, 1H), 6.59 (dd, 1H, J=1.3, 8.0 Hz), 6.65 (d, 1H, J=8.0 Hz), 6.73 (d, 1H, J=1.3 Hz), 7.16–7.35 (m, 10H), 8.34 (s, 1H)

EXAMPLE 11

Synthesis of 4-methyl-2-nitroanisol (1)

A reaction mixture of 2-nitro-p-cresol (23.58 g, 0.154 mmol), methylene chloride (200 ml), tetra-n-butylammonium hydrogensulfate (5.15 g, 15.2 mmol), 1N sodium hydroxide (170 ml) and dimethyl sulfate (16.0 ml, 0.169 mmol) was stirred at room temperature for 2 hours. The reaction mixture was poured into water and extracted with methylene chloride. The organic layer was washed with brine, dried over anhydrous magnesium sulfate and evaporated. The concentrate was immediately used for the next reaction.

Synthesis of 2-methoxy-5-methylaniline (2)

A mixture of the nitro compound (1) obtained above and 10% palladium-carbon (1.00 g, 0.94 mmol) in ethyl acetate (300 ml) was stirred under hydrogen atmosphere at room temperature for 20 hours. Then the palladium-carbon was filtered off, and the solvent was distilled off from the filtrate. The thus-obtained crude product was immediately used for the next reaction.

Synthesis of 4-methyl-2-n-octanoylaminoanisole (3)

To the aniline compound (2) obtained above was added anhydrous n-octanoic acid (48 ml, 0.162 mmol) under ice-cooling, and the mixture was stirred at 0° C.-room temperature for 2 hours. The reaction mixture was poured into a saturated aqueous solution of sodium hydrogencarbonate and extracted with ethyl acetate. The organic layer was washed with brine, dried over anhydrous magnesium sulfate and evaporated. The concentrate was purified by column chromatography on silica gel to give a mixture of the amide compound (3) and anhydrous n-octanoic acid. Yield 55.3 g.

Synthesis of 2-methoxy-5-methyl-N-n-octylaniline (4)

To a solution of the mixture of the amide compound (3) and anhydrous n-octanoic acid obtained above (55.3 g) in dry tetrahydrofran (350 ml) was added dropwise borane-methyl sulfide (10.0–10.2M, 40 ml, 400 mmol) under nitrogen atmosphere under ice-cooling. The reaction mixture was stirred at 0° C. for 30 minutes, at room temperature for 1 hour and then at 60° C. for 4 hours. The reaction mixture was cooled on a ice bath, and water (100 ml) was added thereto. Then 1N hydrochloric acid (300 ml) was added dropwise. The mixture was stirred at room temperature for 1 hour and at 70° C. for 3 hours. The reaction mixture was poured into cooled 4N sodium hydroxide (150 ml) and extracted with ethyl acetate. The organic layer was washed with brine, dried over anhydrous magnesium sulfate and evaporated. The concentrate was purified by column chromatography on silica gel to give the amino compound (4) as colorless liquid. Yield 26.7 g (69%) from 2-nitro-p-cresol.

Synthesis of N-(2-hydroxyethyl)-2-methoxy-5-methyl-N-n-octylaniline (5)

To a solution of the aniline compound (4) (10.0 g, 40.1 mmol) in dry tetrahydrofuran (150 ml) was added dropwise a solution of n-butyllithium in hexane (1.6M, 32.0 ml, 51.2 mmol) under ice-cooling under nitrogen atmosphere. After stirring at the same temperature for 45 minutes, dry HMPA (14 ml) was added thereto, and the mixture was further stirred for 15 minutes. Thereto was added dropwise ethylene oxide (3.0 ml, 60.7 mmol). After being stirred at 0° C.-room temperature for 18 hours, the reaction mixture was poured into water, extracted with ethyl acetate. The extract was washed with brine, dried over anhydrous magnesium sulfate and evaporated. The crude product was purified by column chromatography on silica gel to give the alcohol compound (5) as a yellow oil. Yield 11.6 g (98%).

Synthesis of N-(2-bromoethyl)-2-methoxy-5-methyl-N-n-octylaniline (6)

To a mixture of the alcohol compound (5) (5.26 g, 17.9 mmol) obtained above, dry tetrahydrofuran (150 ml) and carbon 4%trabromide (8.93 g, 26.9 mmol) was added dropwise triphenylphosphine (7.05 g, 26.9 mmol) under ice-cooling under nitrogen atmosphere. The reaction mixture was stirred at 0° C.-room temperature for 3 hours. After the solvent was distilled off, the crude product was purified by column chromatography on silica gel to give the bromo compound (6) as a colorless oil. Yield 3.29 g (72%).

Synthesis of 3-(4-chlorophenyl)-N-(2-methoxy-4-methylphenyl)-N-n-octyl-3-(2-pyridyl)propylamine (Compound 11)

To a mixture of the bromo compound (6) (1.53 g, 4.29 mmol), 2-(p-chlorobenzyl)pyridine (1.31 g, 6.43 mmol), dry xylene (30 ml) and sodium amide (322 mg, 8.25 mmol) was stirred under nitrogen atmosphere at 160° C. for 20 hours. After being cooled to room temperature, the reaction mixture was poured into water and extracted with ethyl acetate. The organic layer was washed with saturated brine, dried over anhydrous magnesium sulfate and evaporated. The concentrate was purified by column chromatography on silica gel to give the chlorophenylamine derivative (Compound 11) as yellow liquid. Yield 682 mg (33%).

IR (neat): 2900, 2830, 1584, 1563, 1490, 1469, 1412, 1226, 1086, 1034, 1011, 795, 743 cm$^{-1}$ $^1$H-NMR (DMSO-d$_6$): δ0.80 (t, 3H, J=6.7 Hz), 1.03–1.36 (m, 12H), 1.94–2.37 (m, 2H), 2.14 (s, 3H), 2.80–3.03 (m, 4H), 3.62 (s, 3H), 4.07 (t, 1H, J=7.5 Hz), 6.62–6.75 (m, 3H), 7.10–7.32 (m, 6H), 7.61 (dt, 1H, J=1.8, 7.6 Hz), 8.47 (dd, 1H, J=1.0, 4.7 Hz)

EXAMPLE 12

Synthesis of 10-(2-hydroxypropyl)phenothiazine (1)

A solution of phenothiazine (5 g, 25.1 mmol) and sodium amide (95%, 1.2 g, 29 mmol) in xylene (30 ml) was heated under reflux for 3 hours. Then propylene oxide (2.5 ml, 37 mmol) was added thereto under ice-cooling, and the reaction mixture was heated under reflux for 3 hours. To the reaction mixture was added water, and the mixture was extracted with chloroform, washed with saturated brine, dried over anhydrous magnesium sulfate and evaporated. The thus-obtained black-brown solution containing xylene was purified by column chromatography on silica gel to give a dark black oil. Yield 4.19 g (65%).

Synthesis of 10-(2-oxopropyl)phenothiazine (2)

To a solution of the compound (1) (2.52 g, 9.79 mmol) obtained above and triethylamine (9.5 ml, 68 mmol) in dimethyl sulfoxide (25 ml) was added a solution of sulfur trioxide-pyridine complex (4.67 g, 29.3 mmol) in dimethyl sulfoxide (25 ml), and the reaction mixture was stirred at room temperature for 30 minutes. To the reaction mixture was added a saturated aqueous solution of sodium hydrogencarbonate, and the mixture was extracted with ethyl acetate. The extract was washed with saturated brine and dried over anhydrous magnesium sulfate. The solvent was distilled off, and thus obtained brown solid was purified by column chromatography on silica gel to give pale green needle-like crystals. Yield 1.93 g (77%).

Synthesis of 2-[1-methyl-2-(phenothiazine-10-yl)ethyl]amino-4-methylphenol (Compound 12)

To a solution of the compound (2) (1.93 g, 7.56 mmol) obtained above, 2-amino-4-methylphenol (1.13 g, 9.18 mmol) in tetrahydrofuran-methanol (1:1) (20 ml) was added sodium cyanoborohydride (95%, 2.0 g, 30 mmol) and the mixture was stirred at room temperature for 1 hour. The reaction mixture was acidified to pH 4–5 with 10% hydrochloric acid in methanol and further stirred for 17 hours. The solvent was distilled off from the reaction mixture. A saturated aqueous solution of sodium hydrogencarbonate was added thereto, and the mixture was extracted with ethyl acetate. The ethyl acetate layer was washed with saturated brine, dried over anhydrous magnesium sulfate and evaporated to give a yellow oil, which was then purified by column chromatography on silica gel to give a pink solid (1.07 g, 2.95 mmol). The thus-obtained solid was recrystallized from ethyl acetate-hexane to give pale pink prismatic crystals. Yield 613 mg (22%). m.p. 185°–187° C.

IR (KBr): 2980, 1600, 1585, 1560 cm$^{-1}$ $^1$H-NMR (DMSO-d$_6$): δ1.20 (d, 3H, J=6 Hz), 2.11 (s, 3H), 3.65–4.00 (m, 2H), 4.08 (dd, 1H, J=6, 13.5 Hz), 4.37 (d, 1H, J=8 Hz), 6.15–6.28 (m, 2H), 6.55 (d, 1H, J=8 Hz), 6.9–7.3 (m, 8H), 8.95 (s, 1H)

EXAMPLE 13

Synthesis of 2-[N-methyl-N-[1-methyl-2-(phenothiazine-10-yl)]ethyl]amino-4-methylphenol (Compound 13)

To a solution of Compound 12 (1.06 g, 2.92 mmol) and 37% formalin (2.2 ml, 29 mmol) in methanol (10 ml) was added sodium cyanoborohydride (95%, 773 mg, 11.7 mmol), and the mixture was stirred at room temperature for 4 hours. The solvent was distilled off from the reaction mixture, saturated brine was added to the residue. The mixture was extracted with chloroform, washed with saturated brine, dried over anhydrous magnesium sulfate and evaporated to give a red-orange oil. The oil was purified by column chromatography on silica gel to give a colorless oil, which was then solidified from hexane to give a colorless solid. Yield 479 mg (43%). m.p. 100°–102° C.

IR (CHCl$_3$): 3380, 3030, 2920, 2840, 1590, 1565 cm$^{-1}$ $^1$H-NMR (DMSO-d$_6$): δ1.04 (d, 3H, J=5 Hz), 2.18 (s, 3H), 2.65 (s, 3H), 3.7–3.98 (m, 2H), 3.98–4.25 (m, 1H), 6.5–6.73 (m, 2H), 6.79 (s, 1H), 6.85–7.3 (m, 8H), 8.44 (bs, 1H)

EXAMPLE 14

Synthesis of 2-acryloylamino-4-methylphenol (1)

To a solution of 2-amino-4-methylphenol (5 g, 40.6 mmol) and pyridine (5 ml, 62 mmol) in methylene chloride (70 ml) was added dropwise a solution of acryloyl chloride (4 ml, 50 mmol) in methylene chloride (30 ml) under ice-cooling. The reaction mixture was stirred at 0° C. for 2 hours. To the reaction mixture was added water, and the mixture was stirred at room temperature for 30 minutes, extracted with methylene chloride, washed with a saturated aqueous solution of sodium hydrogencarbonate and saturated brine and dried over anhydrous magnesium sulfate. The solvent was distilled off, and thus obtained brown oil was purified by column chromatography on silica gel to give a pale yellow prismatic crystals. Yield 1.55 g (22%).

Synthesis of 2-[3-(4-benzhydrylpiperazino)propionyl]amino-4-methylphenol (2)

A solution of the compound (1) (1.52 g, 8.58 mmol) and 1-benzhydrylpiperazine (4.33 g, 17.2 mmol) in ethanol (14 ml) was heated under reflux for 3 hours. The solvent was distilled off from the reaction mixture, water was added to the residue, and the mixture was extracted with ethyl acetate. The ethyl acetate layer was washed with saturated brine, dried over anhydrous magnesium sulfate and evaporated. The residue was purified by column chromatography on silica gel to give a colorless glassy substance (2). Yield 3.47 g (94%).

Synthesis of 2-[3-(4-benzhydrylpiperazino)propyl]amino-4-methylphenol (Compound 14)

Lithium aluminium hydride (606 mg, 16.0 mmol) was added to tetrahydrofuran (25 ml) in several divided portions under ice-cooling, and thereto was added dropwise a solution of the compound (2) (3.43 g, 7.98 mmol) obtained above in tetrahydrofuran (15 ml). The mixture was heated under reflux for 3 hours, and thereto was added water (0.5 ml), 10% sodium hydroxide (0.5 ml) and water (1.0 ml) in that order under ice-cooling. The mixture was stirred at room temperature for 30 minutes. The inorganic substance was removed from the reaction mixture by filtration. The filtrate was dried over anhydrous magnesium sulfate and evaporated to give a yellow-orange glassy substance, which was then purified by column chromatography on silica gel to give a yellow-orange solid. Yield 2.35 g (71%). The thus-obtained solid was recrystallized from ethyl acetate to give colorless needle-like crystals (Compound 14). Yield 987 mg (30%). m.p. 178°–179° C.

IR (KBr): 3400, 3040, 2950, 2830, 1600 cm$^{-1}$ $^1$H-NMR (DMSO-d$_6$): δ1.55–1.8 (m, 2H), 2.12 (s, 3H), 2.2–2.6 (m, 10H), 2.9–3.15 (m, 2H), 4.22 (s, 1H), 4.73 (br, 1H), 6.17 (dd, 1H, J=1.5, 8 Hz), 6.26 (d, 1H, J=1.5 Hz), 6.52 (d, 1H, J=8 Hz), 7.1–7.5 (m, 10H), 8.85 (bs, 1H)

EXAMPLE 15

Synthesis of 2-[3-[4-(4-chlorobenzhydryl)piperazino]propyl]amino-4-methylphenol (Compound 15)

The title compound was obtained in the same manner as in the synthesis of Compound 14 except that 1-(4-chlorobenzhydryl)-piperazine was used in place of 1-benzhydrylpiperazine. m.p. 168°–170° C.

IR (KBr): 3380, 3020, 2920, 2800, 1595, 1520, 1482, 1449, 1211, 1162, 1137, 1083, 998, 786, 756, 718 cm$^{-1}$ $^1$H-NMR (DMSO-d$_6$): δ1.58–1.78 (m, 2H), 2.13 (s, 3H), 2.20–2.55 (m, 10H), 2.96–3.14 (m, 2H), 4.27 (s, 1H), 4.75 (bs, 1H), 6.19 (d, 1H, J=7.8 Hz), 6.27 (d, 1H, J=1.5 Hz), 6.53 (d, 1H, J=7.7 Hz), 7.13–7.46 (m, 9H), 8.90 (bs, 1H)

EXAMPLE 16

Synthesis of 2-[N-[3-(4-benzhydrylpiperazino)propyl]-N-methyl-]amino-4-methylphenol (Compound 16)

To a solution of Compound 14 (597 mg, 1.44 mmol) in tetrahydrofuran-methanol (2:1, 6 ml) was added 37% formalin (1 ml, 13.3 mmol). Sodium cyanoborohydride (286 mg, 4.32 mmol) was added to the mixture while stirring. After being stirred at room temperature for 30 minutes, the reaction mixture was poured into saturated brine and extracted with chloroform. The extract was washed with saturated brine, dried over anhydrous magnesium sulfate and evaporated to give a yellow solid. The solid was purified by column chromatography on silica gel to give a colorless solid (595 mg, 1.39 mmol), which was then recrystallized from ethyl acetate-hexane to give colorless needle-like crystals. Yield 520 mg (84%). m.p. 114°–115° C.

IR (KBr): 3375, 3010, 2940, 2800, 1595, 1580 cm$^{-1}$ $^1$H-NMR (CDCl$_3$): δ1.65–1.85 (m, 2H), 2.24 (s, 3H), 2.2–2.9 (m, 10H), 2.6 (s, 3H), 2.78 (t, 2H, J=6 Hz), 4.24 (s, 1H), 6.7–6.85 (m 3H), 7.1–7.5 (m, 10H)

EXAMPLE 17

Synthesis of 1-(4-chlorobenzhydryl)homopiperazine (1)

A mixture of 4-chlorobenzhydryl chloride (5.32 g, 22.4 mmol), isopropanol (80 ml) and sodium iodide (3.41 g, 22.8 mmol) was stirred at room temperature for 30 minutes. Thereto was added homopiperazine (11.2 g, 112 mmol), and the mixture was stirred at 95° C. for 18 hours. The solvent was distilled off, and the concentrate was poured into a saturated aqueous solution of sodium hydrogencarbonate and extracted with ethyl acetate. The extract was washed with saturated brine, dried over anhydrous magnesium sulfate and evaporated. The thus-obtained crude product was used for the next reaction without purification.

Synthesis of 2-[3-[4-(4-chlorobenzhydryl)homopiperazino)propyl-]amino-4-methylphenol (Compound 17)

Compound 17 was obtained in the same manner as in the synthesis of Compound 14 except that the compound (1) obtained above was used in place of 1-benzhydrylpiperazine.

IR (KBr): 3380, 3020, 3910, 2810, 1600, 1521, 1484, 1453, 1243, 1214, 1162, 1085, 1013, 798, 758, 700 cm$^{-1}$ $^1$H-NMR (DMSO-d$_6$): δ1.67 (quint, 4H, J=6.2 Hz), 2.12 (s, 3H), 2.36–2.77 (m, 10H), 3.00–3.17 (m, 2H), 4.69 (bs, 2H), 6.18 (d, 1H, J=7.8 Hz), 6.29 (d, 1H, J=1.6 Hz), 6.51 (d, 1H, J=7.7 Hz), 7.13–7.53 (m, 9H), 8.90 (bs, 1H)

EXAMPLE 18

Synthesis of 2-[3-(4-hydroxydiphenylmethyl-1-piperidinyl)propyl-]amino-4methylphenol (Compound 18)

Compound 18 was obtained as a yellow amorphous in the same manner as in the synthesis of Compound 14 except that α,α-diphenyl-1-piperidinemethanol was used in place of 1-benzhydrylpiperazine.

IR (KBr): 3310, 3000, 2900, 1595, 1517, 1441, 1245, 1212, 1153, 1060, 961, 790, 742, 696 cm$^{-1}$ $^1$H-NMR (DMSO-d$_6$): δ1.24 (d, 2H, J=11.5 Hz), 1.4–1.6 (m, 2H), 1.67 (quint, 2H, J=6.6 Hz), 1.85 (t, 2H, J=10.7 Hz), 2.13 (s, 3H), 2.30 (t, 2H, J=6.4 Hz), 2.36–2.57 (m, 1H), 2.87 (d, 2H, J=10.5 Hz), 2.94–3.13 (m, 2H), 4.55 (bs, 1H), 5.20 (s, 1H), 6.18 (d, 1H, J=7.7 Hz), 6.28 (d, 1H, J=1.6 Hz), 6.52 (d, 1H, J=7.7 Hz), 7.11 (t, 2H, J=7.2 Hz), 7.25 (t, 4H, J=7.2 Hz), 7.51 (d, 4H, J=7.4 Hz), 8.89 (bs, 1H)

EXAMPLE 19

Synthesis of 2-[3-(4-benzhydryloxy-1-piperidinyl)propyl]amino-4-methylphenol (Compound 19)

Compound 19 was obtained in the same manner as in the synthesis of Compound 14 except that 4-benzhydryloxypiperidine, which had been synthesized by dehydration between 4-hydroxypiperidine and benzhydrol, was used in place of 1-benzhydrylpiperazine. m.p. 114°–115° C.

IR (KBr): 3660–3120, 1596, 1522, 1453, 1452, 1237, 1215, 1090, 1070, 800, 784, 756, 740, 700 cm$^{-1}$ $^1$H-NMR (DMSO-d$_6$): δ1.51–1.77 (m, 4H), 1.80–2.08 (m, 4H), 2.13 (s, 3H), 2.34 (t, 2H, J=6.3 Hz), 2.62–2.82 (m, 2H), 3.04 (t, 2H, J=6.0 Hz), 3.24–3.46 (m, 1H), 4.94 (bs, 1H), 5.62 (s, 1H), 6.17 (dd, 1H, J=1.2, 8.2 Hz), 6.26 (d, 1H, J=1.5 Hz), 6.50 (d, 1H, J=7.7 Hz), 7.16–7.44 (m, 10H), 8.89 (s, 1H)

EXAMPLE 20

Synthesis of 6-tert-butyl-2-[3-[4-(4-chlorobenzhydryl)piperazino]-propyl]amino-4-methylphenol (Compound 20)

Compound 20 was obtained in the same manner as in the synthesis of Compound 14 except that 2-acryloylamino-6-tert-butyl-4-methylphenol, which had been synthesized from 2-amino-6-tert-butyl-4-methylphenol obtained by nitration and reduction of 2-tert-butyl-4-methylphenol, and acryloyl chloride, was used in place of 2-acryloylamino-4-methylphenol, and 1-(4-chlorobenzhydryl)piperazine was used in place of 1-benzhydrylpiperazine.

IR (KBr): 3400, 2995, 2800, 1485, 1450, 1090, 1010, 760 cm$^{-1}$ $^1$H-NMR (DMSO-d$_6$): δ1.32 (s, 9H), 1.70 (quint, 2H, J=6.4 Hz), 2.14 (s, 3H), 2.2–2.5 (m, 10H), 2.98 (t, 2H, J=6.4 Hz), 4.28 (s, 1H), 6.26 (s, 1H), 6.30 (s, 1H), 7.1–7.5 (m, 9H), 8.30 (s, 1H)

EXAMPLE 21

Synthesis of
2-[N-[3-[4-(4-chlorobenzhydryl)piperazino]propyl]-N-isopropyl]amino-4-methylphenol (Compound 21)

Compound 21 was obtained as an oil in the same manner as in the synthesis of Compound 16 except that Compound 15 was used in place of Compound 14 and acetone was used in place of formalin.

IR (neat): 3260, 3020, 2960, 2790, 1598, 1500, 1485, 1452, 1268, 1238, 1153, 1088, 813, 757, 719, 698 cm$^{-1}$ $^1$H-NMR (DMSO-d$_6$): δ0.75 (d, 6H, J=6.4 Hz), 1.20–1.42 (m, 2H), 2.14 (s, 3H), 2.05–2.46 (m, 10H), 2.89 (t, 2H, J=6.6 Hz), 3.19 (sept, 1H), 4.25 (s, 1H), 6.60–6.75 (m, 2H), 6.84 (s, 1H), 7.10–7.47 (m, 9H), 8.09 (bs, 1H)

EXAMPLE 22

Synthesis of
6-tert-butyl-2-[-[3-[4-(4-chlorobenzhydryl)piperazino]-propyl]-N-isopropyl]amino-4-methylphenol (Compound 22)

Compound 22 was obtained as a green amorphous in the same manner as in the synthesis of Compound 21 except that Compound 20 was used in place of Compound 15.

IR (KBr): 3200, 2930, 2790, 1485, 1450, 1235, 1150, 1085, 1010, 755, 695 cm$^{-1}$ $^1$H-NMR (DMSO-d$_6$ 0.5 ml+CDCl$_3$ 0.05 ml): δ0.98 (d, 6H, J=6.4 Hz), 1.20–1.35 (m, 2H), 1.31 (s, 9H), 2.17 (s, 3H), 2.10–2.40 (m, 10H), 2.90 (t, 2H, J=6.8 Hz), 3.0 (sept, 1H, J=6.4 Hz), 4.25 (s, 1H), 6.77 (s, 1H), 6.82 (s, 1H), 7.12–7.42 (m, 9H), 8.15 (bs, 1H)

EXAMPLE 23

Synthesis of
2-[N-[3-(4-hydroxydiphenylmethyl-1-piperidinyl)-propyl]-N-isopropyl]amino-4-methylphenol (Compound 23)

Compound 23 was obtained as an oil in the same manner as in 4he synthesis of Compound 21 except that Compound 18 was used in place of Compound 15.

IR (KBr): 3250, 3000, 2900, 2780, 1591, 1493, 1441, 1375, 1252, 1160, 1059, 961, 807, 721, 695 cm$^{-1}$ $^1$H-NMR (DMSO-d$_6$): δ0.96 (d, 6H, J=6.4 Hz), 1.15–1.52 (m, 6H), 1.83 (bs, 2H), 2.15 (s, 3H), 2.10–2.55 (m, 3H), 2.70–2.85 (m, 2H), 2.89 (t, 2H, J=6.7 Hz), 3.18 (sept, 1H, J=6.5 Hz), 5.21 (s, 1H), 6.64 (d, 1H, J=9.4 Hz), 6.70 (d, 1H, J=9.8 Hz), 6.84 (s, 1H), 7.09 (t, 2H, J=7.2 Hz), 7.23 (t, 4H, J=7.1 Hz), 7.47 (d, 4H, J=7.4 Hz), 8.05 (bs, 1H)

EXAMPLE 24

Synthesis of
4-tert-butyl-2-[3-[4-(4-chlorobenzhydryl)piperazino]-propyl]aminophenol (Compound 24)

Compound 24 was obtained in the same manner as in the synthesis of Compound 14 except that 2-amino-4-tert-butylphenol was used in place of 2-amino-4-methylphenol, and 1-(4-chlorobenzhydryl)piperazine was used in place of 1-benzhydrylpiperazine. m.p. 147° C.

IR (KBr): 3350, 2900, 2790, 1595, 1520, 1480 cm$^{-1}$ $^1$H-NMR (DMSO-d$_6$): δ1.20 (s, 9H), 1.6–1.75 (m, 2H), 2.15–2.5 (m, 10H), 3.0–3.2 (m, 2H), 4.28 (s, 1H), 4.73 (bs, 1H), 6.37 (dd, J=8.0, 1H, 2.1 Hz), 6.46 (d, 1H, J=2.1 Hz), 6.55 (d, 1H, J=8.0 Hz), 7.15–7.5 (m, 9H), 8.94 (bs, 1H)

EXAMPLE 25

Synthesis of
4-tert-butyl-2-[N-[3-[4-(4-chlorobenzhydryl)-piperazino]propyl]-N-isopropyl]aminophenol (Compound 25)

Compound 25 was obtained as an oil in the same manner as in the synthesis of Compound 21 except that Compound 24 was used in place of Compound 15.

IR (CHCl$_3$): 3350, 2920, 2780, 1495, 1480 cm$^{-1}$ $^1$H-NMR (DMSO-d$_6$): δ0.95 (d, 6H, J=6.5 Hz), 1.17 (s, 9H), 1.25–1.4 (m, 2H), 2.1–2.4 (m, 10H), 2.92 (t, 2H, J=6.5 Hz), 3.19 (hept, 1H, J=6.5 Hz), 4.24 (s, 1H), 6.67 (d, 1H, J=8.3 Hz), 6.89 (dd, 1H, J=2.3 Hz), 7.01 (d, 1H, J=2.3 Hz), 7.10–7.45 (m, 9H)

EXAMPLE 26

Synthesis of
2-[3-[4-(4-chlorophenyl)hydroxyphenylmethyl-1-piperidinyl]propyl]amino-4-methylphenol (Compound 26)

Compound 26 was obtained in the same manner as in the synthesis of Compound 18 except that α-4-chlorophenyl-α-phenyl-1-piperidinemethanol was used in place of α,α-diphenyl-1-piperidinemethanol.

IR (KBr): 3350, 3010, 2920, 1598, 1521, 1487, 1444, 1253, 1212, 1151, 1091, 1012, 968, 791, 757, 697 cm$^{-1}$ $^1$H-NMR (DMSO-d$_6$): δ1.24 (t, 2H), 1.40–1.65 (m, 2H), 1.68 (quint, 2H, J=6.8 Hz), 1.87 (t, 2H), 2.13 (s, 3H), 2.32 (t, 2H, J=6.5 Hz), 2.35–2.55 (m, 1H), 2.89 (d, 2H, J=11.1 Hz), 3.03 (t, 2H), 4.55 (bs, 1H), 5.31 (s, 1H), 6.18 (d, 1H, J=7.7 Hz), 6.26 (s, 1H), 6.51 (d, 1H, J=7.7 Hz), 7.13 (t, 1H, J=7.1 Hz), 7.21–7.34 (m, 4H), 7.47–7.57 (m, 4H), 8.84 (brs, 1H)

EXAMPLE 27

Synthesis of
2-[N-[3-[4-(4-chlorophenyl)hydroxyphenylmethyl-1-piperidinyl]propyl]-N-isopropyl]amino-4-methylphenol (Compound 27)

Compound 27 was obtained as an oil in the same manner as in the synthesis of Compound 21 except that Compound 26 was used in place of Compound 15.

IR (Neat): 3300, 3020, 2930, 2800, 1597, 1498, 1483, 1468, 1443, 1380, 1253, 1163, 1088, 1067, 1012, 970, 907, 814, 757, 732 cm$^{-1}$ $^1$H-NMR (CDCl$_3$): δ1.03 (d, 6H, J=6.5 Hz), 1.29–1.58 (m, 6H), 1.80–1.98 (m, 2H), 2.22 (s, 3H), 2.20–2.45 (m, 3H), 2.80–3.00 (m, 4H), 3.08 (sept, 1H, J=6.5 Hz), 6.78 (d, 1H, J=8.1 Hz), 6.85 (d, 1H, J=8.3 Hz), 6.90 (s, 1H), 7.15–7.54 (m, 9H)

EXAMPLE 28

Synthesis of
2-[3-4-[(4-chlorobenzhydryloxy)-1-piperidinyl]propyl]amino-4-methylphenol (Compound 28)

Compound 28 was obtained in the same manner as in the synthesis of Compound 19 except that 4-(4-chlorobenzhydryloxy)piperidine was used in place of 4-benzhydryloxypiperidine. m.p. 104°–106° C.

IR (KBr): 3660–3250, 1600, 1523, 1488, 1452, 1248, 1240, 1216, 1180, 1164, 1136, 1084, 1015, 850, 837, 797, 758, 746, 700 cm$^{-1}$ $^1$H-NMR (DMSO-d$_6$): δ1.48–1.77 (m, 4H), 1.77–1.95 (m, 2H), 1.95–2.10 (m, 2H), 2.13 (s, 3H), 2.34 (t, 2H, J=6.2 Hz), 2.62–2.84 (m, 2H), 3.04 (t, 2H, J=6.1 Hz), 3.17–3.50 (m, 1H), 4.91 (bs, 1H), 5.64 (s, 1H), 6.17 (d,

1H, J=7.9 Hz), 6.26 (s, 1H), 6.51 (d, 1H, J=7.7 Hz), 7.14–7.44 (m, 9H), 8.88 (bs, 1H)

EXAMPLE 29

Synthesis of 2-[3-[4-(4,4'-dichlorobenzhydryl)piperazino]propyl]amino-4-methylphenol (Compound 29)

Compound 29 was obtained in the same manner as in the synthesis of Compound 14 except that 1-(4,4'-dichlorobenzhydryl)piperazine was used in place of 1-benzhydrylpiperazine.

IR (KBr): 3400, 2900, 2800, 1600, 1520, 1480 cm$^{-1}$ $^1$H-NMR (DMSO-d$_6$): δ1.65 (t, 2H, J=6.0 Hz), 2.01 (s, 3H), 2.15–2.5 (m, 10H), 3.01 (t, 2H, J=6.0 Hz), 4.31 (s, 1H), 4.75 (bs, 1H), 6.16 (approx, d, 1H, J=7.7 Hz), 6.24 (approx, s, 1H), 6.49 (d, 1H, J=7.7 Hz), 7.33 (d, 4H, J=8.7 Hz), 7.40 (d, 4H, J=8.7 Hz), 8.88 (bs, 1H),

EXAMPLE 30

Synthesis of 2-[N-[3-[4-(4,4'-dichlorobenzhydryl)piperazino]propyl]-N-isopropyl]amino-4-methylphenol (Compound 30)

Compound 30 was obtained as an oil in the same manner as in the synthesis of Compound 21 except that Compound 29 was used in place of Compound 15.

IR (CHCl$_3$): 2900, 2800, 1490, 1480, 1280 cm$^{-1}$ $^1$H-NMR (DMSO-d$_6$): δ0.94 (d, 6H, J=6.4 Hz), 1.29 (t, 2H, J=6.7 Hz), 2.13 (s, 3H), 2.5–2.0 (m, 10H), 2.88 (t, 2H, J=6.7 Hz), 3.17 (hept, 1H, J=6.4 Hz), 4.28 (s, 1H), 6.63 (d, 1H, J=8.1 Hz), 6.69 (d, 1H, J=8.1 Hz), 6.83 (s, 1H), 7.30 (d, 4H, J=8.8 Hz), 7.37 (d, 4H, J=8.8 Hz),

EXAMPLE 31

Synthesis of 2-[N-[3-(4-benzhydrylpiperazino)propyl]-N-isopropyl]amino-4-methylphenol (Compound 31)

Compound 31 was obtained as an oil in the same manner as in the synthesis of Compound 21 except that Compound 14 was used in place of Compound 15.

IR (CHCl$_3$): 3000, 2960, 2900, 1500 cm$^{-1}$ $^1$H-NMR (DMSO-d$_6$): δ0.96 (d, 6H, J=6.5 Hz), 1.25–1.40 (m, 2H), 2.14 (s, 3H), 2.1–2.45 (m, 10H), 2.90 (t, 2H, J=6.5 Hz), 3.19 (hept, 1H, J=6.5 Hz), 4.20 (s, 1H), 6.65–6.75 (m, 2H), 6.85 (s, 1H), 7.05–7.45 (m, 10H),

EXAMPLE 32

Synthesis of 2-[3-[4-(4,4'-difluorobenzhydryl)piperazino]propyl]amino-4-methylphenol (Compound 32)

Compound 32 was obtained in the same manner as in the synthesis of Compound 14 except that 1-(4,4'-difluorobenzhydryl)piperazine was used in place of 1-benzhydrylpiperazine.

IR (KBr): 3600–2400, 1600, 1500, 1210, 1000, 820 cm$^{-1}$ $^1$H-NMR (DMSO-d$_6$): δ1.55–1.75 (m, 2H), 2.13 (s, 3H), 2.15–2.50 (m, 10H), 3.05 (m, 2H), 4.32 (s, 1H), 6.17 (d, 1H, J=7.7 Hz), 6.25 (s, 1H), 6.51 (d, 1H, J=7.7 Hz), 7.08 (dd, 4H, J=8.8, 8.8 Hz), 7.42 (dd, 4H, J=5.6, 8.8 Hz), 8.90 (bs, 1H)

EXAMPLE 33

Synthesis of 2-[-[3-[4-(4,4'-difluorobenzhydryl)piperazino]propyl]-N-isopropyl]amino-4-methylphenol (Compound 33)

Compound 33 was obtained as an oil in the same manner as in the synthesis of Compound 21 except that Compound 32 was used in place of Compound 15.

IR (Neat): 1730, 1595, 1495, 1220, 1150, 820, 750 cm$^{-1}$ $^1$H-NMR (DMSO-d$_6$): δ0.98 (d, 6H, J=6.4 Hz), 1.25–1.35 (m, 2H), 2.17 (s, 3H), 2.09–2.50 (m, 10H), 2.91 (t, 2H, J=6.7 Hz), 3.20 (six, 1H, J=6.4 Hz), 4.29 (s, 1H), 6.66 (d, 1H, J=8.0 Hz), 6.72 (d, 1H, J=8.0 Hz), 6.85 (s, 1H), 7.08 (dd, 4H, J=8.8, 8.8 Hz), 7.42 (dd, 4H, J=5.6, 8.8 Hz)

EXPERIMENT EXAMPLE 1

Inhibition of lipoperoxide production in rat cerebral tissues (1) Preparation of cerebral tissue homogenate A rat was slaughtered with carbon dioxide, and immediately after blood sampling from the heart, brain was removed and weighed. A 5% (7/v) tissue homogenate was prepared by a homogenizer with PBS (pH 7.3). Homogenation was conducted two times for 15 seconds (scale 10) while cooling.

(2) Inhibition of lipoperoxide production in rat cerebral 4issues.

Each of the test drugs (50 μl, concentration 10, 1, 0.1, 0.01, 0.001 μg/ml) was placed in a polypropylene tube, to which was added cerebral tissue homogenate (1 ml), followed by incubation at 37° C. in a thermobath for 120 minutes. Thereafter, 1% phosphoric acid (0.3 ml), 10% phosphotungstic acid (0.2 ml) and 0.67% TBA (tiobarbituric acid) agent (1 ml) were added thereto while stirring as necessary, and immediately thereafter, TBA reaction was conducted in a boiling water bath for 20 minutes. The mixture was cooled in ice water for 5 minutes, and added with n-butanol (4 ml). After 10 minutes' shaking extraction, it was centrifuged at 3000 rpm and at room temperature (low temperature causes change of absorbance) for 10 minutes. The absorbance of the butanol layer (upper layer) was measured at a wavelength of 535 nm. The difference between the absorbance of the control incubated at 37° C. (added with dimethylsulfoxide only) and that of the control cooled at 2° C. (added with dimethylsulfoxide only) was taken as the amount of 100% lipoperoxide production, and the percent suppression of the drug was calculated from the following formula.

$$\% \text{ Inhibition} = \frac{A - B}{A} \times 100$$

wherein A is the difference of absorbance of 37° C. control and 2° C. control, and B is the difference of absorbance of a drug sample and 2° C. control. The IC$_{50}$ (μg/ml) was calculated by least square method using the percent inhibition at each concentration.

TABLE 1

| Compound | IC$_{50}$ (μg/ml) |
| --- | --- |
| 1 | 0.39 |
| 5 | 0.20 |
| 6 | 0.31 |
| 7 | 0.16 |
| 10 | 0.23 |

TABLE 1-continued

| Compound | IC$_{50}$ (μg/ml) |
| --- | --- |
| 12 | 0.086 |
| 14 | 0.038 |
| 15 | 0.12 |
| 16 | 0.30 |
| 17 | 0.013 |
| 18 | 0.029 |
| 19 | 0.036 |
| 20 | 0.066 |
| 21 | 0.44 |
| 23 | 0.79 |
| 26 | 0.04 |
| 32 | 0.10 |

EXPERIMENT EXAMPLE 2

Effect on TPA-induced mouse ear edema test

Male ICR mice weighing about 20 g were etherized, and fixed at the dorsal position. TPA (12-O-tetradecanoylphorbol-13-acetate: phorbol 12-myristate-13-acetate, 1 μg/20 μl) dissolved in a mixed solution of acetone: pyridine: water (97:2:1) was coated on the left year while drying with a dryer. Five hours later, the mice were slaughtered by vertebral dislocation. The both ears were stamped out with a circle chisel (punch), and weighed. The weight difference between the both ears was taken as an index of the degree of edema, and the percent inhibition was calculated from the comparison with the control. Each drug was dissolved in TPA solution (100 μg/20 ml).

TABLE 2

| Compound | Inhibition (%) |
| --- | --- |
| 3 | 71.1 |
| 4 | 75.0 |
| 5 | 75.0 |
| 6 | 62.7 |
| 7 | 54.6 |
| 12 | 74.7 |
| 14 | 77.8 |
| 15 | 86.7 |
| 16 | 50.9 |
| 17 | 87.0 |
| 18 | 89.0 |
| 19 | 85.5 |
| 20 | 63.8 |
| 21 | 44.4 |
| 23 | 39.2 |
| 26 | 97.5 |
| 32 | 64.1 |

Formulation Example 1: Tablets

| (1) Compound of the invention (I) | | 10 mg |
| --- | --- | --- |
| (2) Fine particle No. 209 for direct compression (Fujui Kagaku) | | 46.6 mg |
| magnesium metasilicate aluminate | 20% | |
| corn starch | 30% | |
| lactose | 50% | |
| (3) Crystalline cellulose | | 24.0 mg |
| (4) Carboxylmethylcellulose · calcium | | 4.0 mg |
| (5) Magnesium stearate | | 0.4 mg |

(1), (3) and (4) were respectively passed through a 100-mesh sieve in advance. (1) and (3), and (4) and (2) were respectively dried to a certain water content, after which kneaded in a kneader at the above-mentioned weight ratio. To the homogeneous powder mixture was added (5), followed by mixing for a short time (30 sec.), and the mixture was compressed (pounder: 6.3 mm φ, 6.0 mmR) to give tablets of 85 mg per tablet.

The tablets obtained may be coated with a conventional enteric coating film (e.g. polyvinylacetaldiethylaminoacetate) or edible coloring agents.

Formulation Example 2: Capsules

| (1) Compound of the invention (I) | 50 g |
| --- | --- |
| (2) Lactose | 935 g |
| (3) Magnesium stearate | 15 g |

The above ingredients were weighted and homogeneously mixed. The powder mixture was charged in a hard gelatin capsule by 200 mg per capsule.

Formulation Example 3: Injections

| (1) Compound of the invention (I) · hydrochloride | 5 mg |
| --- | --- |
| (2) Sucrose | 100 mg |
| (3) Physiological saline | 10 ml |

The mixture of the above ingredients was filtered through a membrane filter, subjected to sterilization by filtration, and the filtrate was aseptically charged in a vial, which was filled with nitrogen gas. The vial was sealed to give an intravenous injection.

Formulation Example 4: Ointments

| (1) Compound of the invention (I) | 1 g |
| --- | --- |
| (2) Plastibase | 99 g |

The compound of the invention (I) was dissolved in anhydrous ethanol (10 g), and added to plastibase which had been heated to about 60° C., followed by stirring for dissolution. After the mixture became homogeneous, the ethanol was removed under reduced pressure, and the mixture was cooled to room temperature to give an ointment.

What is claimed is:

1. An aminophenol derivative which is represented by the formula

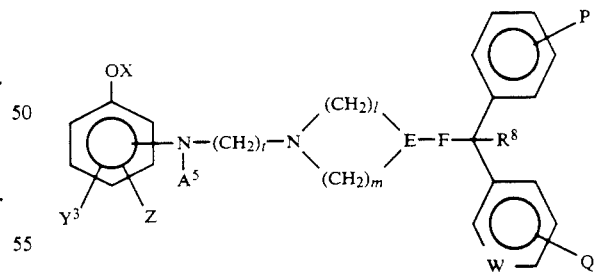

wherein X is a hydrogen atom, $Y^3$ is a hydrogen atom or lower alkyl, Z is a hydrogen atom, lower alkyl, halogen atom or trifluoromethyl, $A^5$ is a hydrogen atom or lower alkyl, t is an integer of 1 to 5, l and m are each an integer of 2 or 3, with the sum of l and m being 4 or 5, E and W are the same or different and each is a nitrogen atom or CH, F is a direct bond or oxygen atom, P and Q are the same or different and each is a hydrogen atom, halogen atom, lower alkyl or lower alkoxy, and $R^8$ is a hydrogen atom, hydroxyl group or a hydroxy-protecting group, or its pharmacologically acceptable salt.

2. An aminophenol derivative or its pharmacologically acceptable salt according to claim 1, wherein N is bound at the ortho-position and $Y^3$ is bound at the para-position relative to the OX.

3. A pharmaceutical composition containing an aminophenol derivative or its pharmacologically acceptable salt of claim 1 as an active ingredient and a pharmacologically acceptable additive.

4. An aminophenol derivative according to claim 1, which is selected from the group consisting of 2-[3-(4-benzhydrylpiperazino)propyl]amino-4-methylphenol, 2-[3-[4-(4-chlorobenzhydryl)piperazino]propyl]amino-4-methylphenol, 2-[N-[3-(4-benzhydrylpiperazino)propyl]-N-methyl]amino-4-methylphenol, 2-[3-[4-(4-chlorobenzhydryl)homopiperazino]propyl]amino-4-methylphenol, 2-[3-(4-hydroxydiphenylmethyl-1-piperidinyl)propyl]amino-4-methylphenol, 2-[3-(4-benzhydryloxy-1-piperidinyl)propyl]amino-4-methylphenol, 2-tert-butyl-6-[3-[4-(4-chlorobenzhydryl)piperazino]propyl]amino-4-methylphenol, 2-[N-[3-[4-(4-chlorobenzhydryl)piperazino]propyl]-N-isopropyl]amino-4-methylphenol, 6-tert-butyl-2-[N-[3-[4-(4-chlorobenzhydryl)piperazino]propyl]-N-isopropyl]amino-4-methylphenol, 2-[N-[3-(4-hydroxydiphenylmethyl-1-piperidinyl)propyl]-N-isopropyl]amino-4-methylphenol, 4-tert-butyl-2-[3-[4-(4-chlorobenzhydryl)piperazino]propyl]aminophenol, 4-tert-butyl-2-[N-[3-[4-(4-chlorobenzhydryl)piperazino]propyl]-N-isopropyl]aminophenol, 2-[3-[4-(4-chlorophenyl)hydroxyphenylmethyl-1-piperidinyl]propyl]amino-4-methylphenol, 2-[N-[3-[4-(4-chlorophenyl)hydroxyphenylmethyl-1-piperidinyl]propyl]-N-isopropyl]amino-4-methylphenol, 2-[3-[4-(4-chlorobenzhydryloxy)-1-piperidinyl]propyl]amino-4-methylphenol, 2-[3-[4-(4,4'-dichlorobenzhydryl)piperazino]propyl]amino-4-methylphenol, 2-[N-[3-[4-(4,4'-dichlorobenzhydryl)piperazino]propyl]-N-isopropyl]amino-4-methylphenol, 2-[-[3-(4-benzhydrylpiperazino)propyl]-N-isopropyl]amino-4-methylphenol, 2-[3-[4-(4,4'-difluorobenzhydryl)piperazino]propyl]amino-4-methylphenol, and 2-[N-[3-[4-(4,4'-difluorobenzhydryl)piperazino]propyl]-N-isopropyl]amino-4-methylphenol.

5. A method for inhibiting production of active oxygens or trapping active oxygens, comprising administering a pharmacologically effective amount of the pharmaceutical composition of claim 3 to an animal host needing to inhibit the production of active oxygens or trap active oxygens.

6. A method for treating inflammation, comprising administering a pharmacologically effective amount of the pharmaceutical composition of claim 3 to an animal host in need of treatment for inflammation.

7. A method for treating allergies, comprising administering a pharmacologically effective amount of the pharmaceutical composition of claim 3 to an animal host in need of treatment for allergies.

* * * * *